United States Patent
Bonacchi et al.

(10) Patent No.: US 9,616,141 B2
(45) Date of Patent: Apr. 11, 2017

(54) SILICA NANOPARTICLES DOPED WITH MULTIPLE DYES FEATURING HIGHLY EFFICIENT ENERGY TRANSFER AND TUNABLE STOKES-SHIFT

(75) Inventors: Sara Bonacchi, Bologna (IT); Marco Montalti, Bologna (IT); Luca Prodi, Bologna (IT); Nelsi Zaccheroni, Bologna (IT); Riccardo Juris, Bologna (IT); Damiano Genovese, Bologna (IT); Enrico Rampazzo, Bologna (IT)

(73) Assignee: ALMA MATER STUDIORUM UNIVERSITA DI BOLOGNA, Bologna (IT)

( * ) Notice: Subject to any disclaimer, the term of this patent is extended or adjusted under 35 U.S.C. 154(b) by 591 days.

(21) Appl. No.: 13/879,408

(22) PCT Filed: Oct. 13, 2011

(86) PCT No.: PCT/IB2011/054546
§ 371 (c)(1),
(2), (4) Date: Aug. 12, 2013

(87) PCT Pub. No.: WO2012/049657
PCT Pub. Date: Apr. 19, 2012

(65) Prior Publication Data
US 2013/0315835 A1 Nov. 28, 2013

(30) Foreign Application Priority Data
Oct. 14, 2010 (IT) .............................. RM2010A0547

(51) Int. Cl.
*A61K 49/00* (2006.01)
*G01N 33/533* (2006.01)
(52) U.S. Cl.
CPC ...... *A61K 49/0093* (2013.01); *A61K 49/0021* (2013.01); *A61K 49/0032* (2013.01); *A61K 49/0039* (2013.01); *A61K 49/0041* (2013.01); *G01N 33/533* (2013.01)

(58) Field of Classification Search
USPC ......................................................... 424/9.6
See application file for complete search history.

(56) References Cited

U.S. PATENT DOCUMENTS

2009/0035576 A1* 2/2009 Prasad ............... A61K 49/0021
428/402

FOREIGN PATENT DOCUMENTS

WO 2010013136 A2 2/2010
WO 2010013137 A1 2/2010

OTHER PUBLICATIONS

Chi et al., J. Phys. Chem. C 2010, 114, 2519-2523 (Published on Web Jan. 22, 2010).*
ISR in corresponding PCT application PCT/IB2011/054546.
Rampazzo et al., "Energy Transfer from Silica Core-Surfactant Shell Nanoparticles to Hosted Molecular Fluorophores", J. Phys Chem., vol. 114, Jul. 13, 2010.
Montalti et al., "Energy Transfer in Fluorescent Silica Nanoparticles,", Langmuir, vol. 20, Mar. 3, 2004, pp. 2989-2991.

* cited by examiner

*Primary Examiner* — Michael G Hartley
*Assistant Examiner* — Robert Cabral
(74) *Attorney, Agent, or Firm* — Kristina Castellano; Castellano PLLC

(57) ABSTRACT

The present invention relates to silica nanoparticles comprising at least two dyes. Said dyes have a respective relationship of donor-acceptor couple in an energy transfer process and have a molar absorption coefficient ≥10,000 $M^{-1}$ $cm^{-1}$ for the considered spectral region, a fluorescence quantum yield ≥0.01, good overlap integral, according to the Förster theory, between said donor and said acceptor dye; said active compounds may be lipophilic or may present a functionality useful for the introduction of a trialkoxysilane moiety. The dyes provide an efficient energy transfer process. Said nanoparticles are useful as probes in the field of medicine, in particular therapy and diagnostics, more particularly in theranostics, and in the field of analytical chemistry.

9 Claims, 7 Drawing Sheets

SILICA NANOPARTICLES DOPED WITH MULTIPLE DYES FEATURING HIGHLY EFFICIENT ENERGY TRANSFER AND TUNABLE STOKES-SHIFT

CLAIM FOR PRIORITY

This application is a U.S. National Stage Application of PCT/IB2011/054546 filed on Oct. 13, 2011, which claims priority to Italian patent application RM2010A000547 filed on Oct. 14, 2010, the contents of both of which are incorporated herein by reference.

The present invention relates to the field of nanotechnology, in particular to silica nanoparticles comprising at least two dyes. More in particular, the present invention relates to silica nanoparticles wherein the dyes provide an efficient energy transfer process. The present invention also provides the use of said nanoparticles in the field of medicine, in particular therapy and diagnostics, more particularly in theranostics, and in the field of analytical chemistry.

BACKGROUND OF THE INVENTION

Luminescent dyes are widely used markers for many applications in fields of high impact such as environmental and food analysis, security, and medical diagnostics. Fluorescence measurements are usually very sensitive, low cost, easily performed, and versatile, offering submicron visualisation and sub millisecond temporal resolution (L. Prodi, *New J. of Chem.* 2005, 29, 20-31).

In particular, since an early diagnosis is strictly connected to the success of the therapy and to the quality of life of the patient, medical diagnostics requires luminescent labels and sensors endowed with specific (photo)chemical and photophysical properties, including water solubility, photostability, very low toxicity and high brightness (L. Prodi, *New J. of Chem.* 2005, 29, 20-31; Wolfbeis, O. S. *Analytical Chemistry* 2006, 78, 3859).

The versatility of photoluminescence spectroscopy originates also from the wide number of parameters that can be tuned in order to optimize the convenient signal. Even very complex analytical problems can be indeed overcome by controlling the excitation and emission wavelengths, the time window of signal collection, and the polarization of the excitation beam or of the emitted light.

A valuable fluorescence-based label must present different features (O. S. Wolfbeis, *Anal. Chem.* 2006, 78, 3859-3873). As all bio-labels, it is requested to present reactive groups for the covalent coupling to biomolecules, to be water soluble and non toxic. As far as the fluorescent properties are concerned, the first one relies on the fact that the fluorescent unit should give the highest possible luminescence signal. Reminding that photoluminescence is a two-steps process, since it involves the formation of the excited state through the absorption of a photon and its consequent radiative deactivation, the signal intensity is directly related to the efficiency of both processes through the molar absorption coefficient ($\epsilon$) and the luminescence quantum yield ($\Phi$). The luminescence intensity in fact, in very diluted solutions is directly proportional to the product $\epsilon \times \Phi$, that is defined as the brightness of the dye (L. Prodi, ibid.). Photostability is also particularly important, especially in imaging applications. Furthermore, autofluorescence and light scattering, sources of relevant interferences particularly when biological samples are involved, have to be avoided in order to increase the signal-to-noise ratio. This can be done typically using three distinct approaches. The first one is based on the development and use of red and Near Infra-Red (NIR) dyes, that show absorption and luminescence bands in the 700-900 nm region. These dyes offer minimal background as a result of reduced scattering (due to the inverse $4^{th}$ power dependence on the wavelength) and of the absence of natural fluorescence of biomolecules in this spectral range. The second approach is based on the use of phosphorescent dyes with long lifetimes at room temperature. In this case, the background light is excluded by the use of time-resolved spectroscopy, since the scattered light and the fluorescence from natural fluorophores decay much faster than phosphorescence, and can be therefore eliminated by the measuring arrangement. Finally, a large Stokes-shift can also be of value, since it helps to reduce the interferences from the Rayleigh-Thyndall and Raman bands.

Because of the wide application of luminescence spectroscopy, huge research efforts have been spent to optimize the design of fluorescent labels, also taking profit of the advances in the nanotechnology arena (Bruchez, M.; Moronne, M.; Gin, P.; Weiss, S.; Alivisatos, A. P. *Science* 1998, 281, 2013; Riehemann, K.; Schneider, S. W.; Luger, T. A.; Godin, B.; Ferrari, M.; Fuchs, H. *Angew. Chem. Int. Edit.* 2009, 48, 872; Shi, D. L. *Adv. Funct. Mater.* 2009, 19, 3356; Gunasekera, U. A.; Pankhurst, Q. A.; Douek, M. *Targeted Oncology* 2009, 4, 169; Strassert, C. A.; Otter, M.; Albuquerque, R. Q.; Hone, A.; Vida, Y.; Maier, B.; De Cola, L. *Angew Chem Int Edit* 2009, 48, 7928, Doshi, N.; Mitragotri, S. *Adv. Funct. Mater.* 2009, 19, 3843; Medintz, I. L.; Uyeda, H. T.; Goldman, E. R.; Mattoussi, H. *Nature Materials* 2005, 4, 435). Among all the different possibilities offered by this research field, silica based luminescent nanoparticles (also known as Dye Doped Silica Nanoparticles—DDSNs) can offer intriguing solutions for important analytical problems, particularly those related to medical diagnostics and imaging (D. Shi, *Adv. Funct. Mat.* 2009, 19, 3356-3373), and for the development of nanotheranostic devices (Shi, D. L. *Adv. Funct. Mater.* 2009, 19, 3356; Gunasekera, U. A.; Pankhurst, Q. A.; Douek, M. *Targeted Oncology* 2009, 4, 169; Yong, K. T.; Roy, I.; Swihart, M. T.; Prasad, P. N. *Journal of Materials Chemistry* 2009, 19, 4655; Kim, D. K.; Dobson, J. *Journal of Materials Chemistry* 2009, 19, 6294; Liu, Y. Y.; Miyoshi, H.; Nakamura, M. International *Journal of Cancer* 2007, 120, 2527; Liu, Y.; Lou, C.; Yang, H.; Shi, M.; Miyoshi, H. Curr. *Cancer Drug Targets* 2011, 11, 156). Silica, in fact, does not present intrinsic toxicity, although deeper investigations are underway to completely rule out possible hazards related to the tiny dimensions of nanoparticles (Gunasekera, U. A.; Pankhurst, Q. A.; Douek, M. *Targeted Oncology* 2009, 4, 169; Wang, L.; Wang, K. M.; Santra, S.; Zhao, X. J.; Hilliard, L. R.; Smith, J. E.; Wu, J. R.; Tan, W. H. *Analytical Chemistry* 2006, 78, 646; Yong, K. T.; Roy, I.; Swihart, M. T.; Prasad, P. N. Journal of *Materials Chemistry* 2009, 19, 4655; Burns, A. A.; Vider, J.; Ow, H.; Herz, E.; Penate-Medina, O.; Baumgart, M.; Larson, S. M.; Wiesner, U.; Bradbury, M. *Nano Letters* 2009, 9, 442). Moreover, their quite simple and affordable synthesis can easily lead to water-soluble systems ready for bio-conjugation. In addition, each DDSN can contain many fluorophores and reach a molar absorption coefficient that easily overcomes $10^6 \text{ M}^{-1} \text{ cm}^{-1}$. The silica matrix can also protect the dyes segregated inside the nanoparticle from external chemicals, thus increasing their (photo)stability and, in many cases, their luminescence quantum yield, so that DDSNs generally show impressively high brightness.

Besides brightness, however, DDSNs can present also the other features discussed above.

For example they can be easily engineered to present a large Stokes-shift and, in more demanding conditions, to present suitable properties for barcoding and multiplexing analysis. The simplest strategy proposed so far for obtaining a large separation between excitation and emission wavelength is the one used by Wiesner and coworkers (E. Herz, A. Burns, D. Bonner, U. Wiesner, *Macromol. Rapid Commun.* 2009, 30, 1907-1910), who synthesised DDSNs containing commercial fluorophores characterized by an intrinsic large Stokes shift (typically having the lowest excited state with a charge transfer character) and derivatized with an alkoxysilane group. This approach is straightforward but may be limited by the relatively small amount of dyes with this property.

Another, most interesting and fruitful approach is to exploit efficient energy transfer processes between two or more species, metal complexes or organic dyes, that are confined inside the silica nanoparticle. Zhao and co-workers (C. Wu, J. Hong, X. Guo, C. Huang, J. Lai, J. Zheng, J. Chen, X. Mu, Y. Zhao, *Chem. Commun.* 2008, 750-752) developed a silica based system doped with Ru(II) and Tb(III) complexes, while Konovalov and co-workers (S. V. Fedorenko, O. D. Bochkova, A. R. Mustafina, V. A. Burilov, M. K. Kadirov, C. V. Holin, I. R. Nizameev, V. V. Skripacheva, A. Yu. Menshikova, I. S. Antipin, A. I. Konovalov, *J. Phys. Chem. C* 2010, 114, 6350-6355) proposed an analogous system, but even more red shifted, based on species containing Ru(II) and Yb(III).

This strategy can also allow to obtain a set of nanoparticles presenting emissions of different colours, but that can be efficiently excited at the same wavelength (L. Wang, W. H. Tan, *Nano Lett.* 2006, 6, 84-88; L. Wang, C. Y. Yang, W. H. Tan, *Nano Lett.* 2005, 5, 37-43; X. L. Chen, M. C. Estevez, Z. Zhu, Y. F. Huang, Y. Chen, L. Wang, W. H. Tan, *Anal. Chem.* 2009, 81, 7009-7014), a feature that is otherwise achievable only using Quantum Dots (QDs). It is important to note that, depending on the number and nature of the dyes and the efficiency of the energy transfer processes among them, two different applications can be figured out.

The first one is based on the development of barcoding NPs. In this case, a family of different nanoparticles is prepared using a set of n dyes, each one giving distinguishable luminescence band, as doping material. Each kind of nanoparticle is characterized by a different concentration of the various dyes inside the silica matrix. If the dyes are suitably chosen in order to have a partial but not complete energy transfer, all nanoparticles can exhibit a multiband emission under one wavelength excitation, and they can be distinguished by a signature constituted by different intensities at the n bands (colours) of the different n dyes. Using NPs doped with four dyes presenting 5 different intensities at each of the four emission bands, 1024 ($4^4$) different nanoparticles can be envisaged. This approach is of help whenever a single nanoparticle can be addressed, for example in fluorescence microscopy or flow-cytometry: if each kind of nanoparticle is derivatized in order to recognize a different biomolecules or biostructure (cell), the fluorescence signature of the NPs indicates unambiguously the nature of the analyte under investigation, allowing extensive multiplexing. It is important to remind that the ability to simultaneously measure the amount of many analytes in a single assay, is becoming more and more important in medical diagnostics and imaging (Wolfbeis, O. S. *Analytical Chemistry* 2006, 78, 3859; Yao, G.; Wang, L.; Wu, Y. R.; Smith, J.; Xu, J. S.; Zhao, W. J.; Lee, E. J.; Tan, W. H. *Analytical and Bioanalytical Chemistry* 2006, 385, 518; Sukhanova, A.; Nabiev, I. *Critical Reviews in Oncology Hematology* 2008, 68, 39). Many examples are reported of this approach also for silica nanoparticles.

The second approach is possible only when a (almost) complete energy transfer occurs between the different dyes present inside the nanoparticle. If a set of four different dyes, A, B, C, and D (in order of increasing wavelength) are used, a set of four nanoparticles can be obtained containing (i) A, (ii) A and B, (iii) A, B, and C and (iv) A, B, C, and D. All nanoparticles could be excited at the absorption of A (single wavelength excitation) but, in this case, only the longest-wavelength dye can exhibit significant fluorescence even at short-wavelength excitation (Wang, L.; Tan, W. H. *Nano Letters* 2006, 6, 84). Although in this case the number of possible analytes that can be investigated at the same time is significantly lower, it is possible to distinguish the different signals also without the need to separate the different nanoparticles, a feature that is of interest, for example, in many DNA analysis, cytofluorimetry and histochemistry. In this context, DDSNs can be a valuable alternative to the commercial Tandem Dyes, that are a combination of two fluorochromes, an energy donor, such as phycoerythrin, and an energy acceptor (typically Cyanine 5 or 7) (Roederer, M.; Kantor, A. B.; Parks, D. R.; Herzenberg, L. A. *Cytometry* 1996, 24, 191).

Tandem dyes, while offering high brightness and large Stokes-shifts, presents many drawbacks, such as instability and variability (Hulspas, R.; Dombkowski, D.; Preffer, F.; Douglas, D.; Kildew-Shah, B.; Gilbert, J. *Cytom. Part A* 2009, 75A, 966).

There is also the need to provide highly reproducible and stable labels based on silica nanoparticles doped with (at least) two different dyes in which a very efficient energy transfer process between them could ensure an almost quantitative quenching of the donor and sensitization of the acceptor.

It is also to note that a proper design of efficient intraparticle energy transfer could yield DDSNs suitable to perform other highly valuable functions such as light harvesting, signal processing and energy conversion (Bonacchi, S.; Genovese, D.; Juris, R.; Montalti, M.; Prodi, L.; Rampazzo, E.; Zaccheroni, N. *Angew. Chem. Int. Ed.* 2011, 50, 4056). To our knowledge, this kind of approach is still unexplored in the field of silica nanoparticles.

Nanoparticles are used in the bio-analytical field, in particular for the detection, labelling and imaging of biomolecules and also as therapeutics, especially as drug carriers (see for example Q. Huo, J. Liu, L. Q. Wang, Y. Jiang, T. N. Lambert, E. Fang, *J. Am. Chem. Soc.* 2006, 128, 6447-6453).

Tan and co-workers (L. Wang, W. Tan, *Nano Lett.* 2006, 6, 84-88 and in WO2007044711) disclose dual- and triple-dye nanoparticles for detection of microorganisms and biological material. According to these references, one other potential advantage of Fluorescence Energy Transfer Process (FRET) NPs is that by optimizing the amount of dye molecules in an NP, the emission spectrum can be tuned so that only the longest-wavelength dye will exhibit significant fluorescence at a short-wavelength excitation. This feature will overcome the challenge of the small Stokes shift of many organic dyes, enabling the NPs to be detected in samples with significant Rayleigh/Raman scattering or with endogenous fluorescece. However there are no indications on how to find a solution to this problem or to provide any improvement. Moreover, energy transfer efficiencies are lower and the "noise" of the channels different from the main one is high. By this reason, the authors suggest application also in bar-coding, where for each channel (colour) there are different intensities (for example 4, which with 5 channels give $5^4$ (1024) kinds of different nanoparticles, each one can be associated with a given biomarker). This kind of application is unsuitable for the purposes of the present invention.

L. Wang, W. Zhao, W. Tan, *Nano Res.* 2008, 1, 99-115 review the use of bioconjugated silica nanoparticle in therapy and diagnostics. In this review, the authors propose two- and three-dye doped silica nanoparticle for multiplexed bacteria detection. A three dye nanoparticle is described, the three dyes were chosen to allow efficient fluorescence energy transfer and are fluorescein isothiocyanate (FITC), rhodamine 6G (R6G) and 6-carboxyl-X-rhodamine (ROX) because of their effective spectral overlapping.

A number of diagnostic techniques using Energy Transfer Process (or Fluorescence Energy Transfer Process—FRET) require high brightness associated with a large Stokes shift.

This implies the highest possible efficiency for energy transfer process, the possibility of single wavelength excitation and large Stokes shift.

However, there is still the problem of parasite self-quenching of the donor dye.

Furthermore, in the search of the highest brightness possible, self-quenching processes have to be minimized, since they reduce the average fluorescence quantum yield limiting the validity of the direct approach to increasing the molecule brightness by increasing the extent of labelling (Lakowicz, J. R. Principles of Fluorescence Spectroscopy; 3rd Ed. ed.; Springer: New York, 2006; Montalti, M.; Prodi, L.; Zaccheroni, N.; Zattoni, A.; Reschiglian, P.; Falini, G. *Langmuir* 2004, 20, 2989).

In this context, it has to be underlined that also inside DDSNs self-quenching processes can occur, although the observed decrease in the quantum yield is often more than counterbalanced by the increase of the absorption due to the high number of dyes included in the core of the nanoparticles. Efficient energy transfer inside DDSNs can help in this direction.

In particular, coumarinic dyes, or xanthene dyes such as fluorescein, are good donors in energy transfer process, but suffer of parasite self-quenching when loaded in nanoparticles in particular concentrations (see for example: M. Montalti, L Prodi, N. Zaccheroni, A. Zattoni, P. Reschiglian, G. Falini, *Langmuir,* 2008, 20, 2989-2991).

As far as known to the present inventors, the solution to the problem of self-quenching and at the same time assuring an efficient energy transfer process and a large Stokes shift in multiplexing analytical and diagnostic techniques has not yet been reported in the literature.

SUMMARY OF THE INVENTION

It has surprisingly been found that using certain silica nanoparticles disclosed in WO2010013136 and WO2010013137 in combination with a selection of dyes endowed with specific spectral characteristics, the problem of self-quenching is unexpectedly avoided or at least substantially reduced, and a large Stokes shift is obtained even using a single excitation wavelength. At the same time only the longest wavelength dye exhibits significant fluorescence even at the shorter excitation wavelength.

One of the advantages of the present invention is to provide, among others advantages, mono-, bi-, tri- and tetra-chromophoric nanoparticles, observing unprecedented efficiencies for the energy transfer processes between the different dyes inside the nanostructures. These processes lead, from one side, to a very high overall sensitization, and, from the other side, to a very low residual emission of the different donors, allowing obtaining with single wavelength excitation at least four different colours with almost no cross interferences.

Therefore, it is an object of the present invention a silica nanoparticle comprising:
a. a micelle, said micelle having a substantially hydrophilic shell and a substantially hydrophobic central portion;
b. a core, which is located in the area of the micelle central portion and comprises a silicate network;
c. a plurality of molecules of at least a surfactant, which molecules comprise at least a molecule of a functionalized surfactant having the following structure:

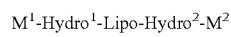

wherein
Lipo represents a substantially hydrophobic chain,
Hydro$^1$ and Hydro$^2$ represent, independently of each other, a respective substantially hydrophilic chain;
M$^1$ is a recognition functionality;
M$^2$ is selected from the group consisting of: —H, —OH, a recognition functionality and a hetero group;
d. a first and at least a second dye; wherein said first and said at least second dyes are a dye with the respective relationship of donor-acceptor couple in an energy transfer process and have a molar absorption coefficient $\epsilon \geq 10{,}000$ M$^{-1}$ cm$^{-1}$, for the considered spectral region, a fluorescence quantum yield $\phi \geq 0.01$, good overlap integral, according to the Förster theory, between said donor and said acceptor dye; said dyes may be lipophylic (insoluble in water) or may present a functionality (for example amine, —COOH, —N$_3$, alkyne, alkene, acryloyl, —SH, maleimide, aldehyde, —OH, isothiocyanate, sulfonyl chloride, iodoacetyl, TCT (2,4,6-Trichloro-1,3,5-triazine) or an activated carboxylic group such as NHS and NHS-sulfo esters (N-hydroxysuccinimide and sulfo N-hydroxysuccinimide), TFP ester (2,3,5,6-Tetrafluorophenol), PFP ester (pentafluorophenol), HOBt ester (1-hydroxybenzotriazole), N-acylimidazole) useful for the introduction of a trialkoxysilane moiety.

Another object of the present invention is the use of the above nanoparticle in therapy, diagnostics and theranostics. A particularly preferred use of the nanoparticle of the present invention is a probe, according to the definitions as commonly intended in this technical field and also according to the definitions provided in the above mentioned WO2010013136 and WO2010013137.

Another object of the present invention is the use of the above nanoparticle in analytical chemistry, in particular as a probe as commonly intended in this technical field.

Another object of the present invention is a diagnostic or theranostic composition comprising a suitable amount of the above nanoparticle.

The nanoparticles of the present invention present the advantage that energy transfer efficiency of each couple of donor/acceptor and the of overall series of dyes is ≥85%.

The present invention provides the following further advantages:
very high overall sensitization and very low residual emission of the different donors, when the nanoparticle contains more than two dyes;
very large Stokes shifts, of up to 700-800 nm;
very high brightness even exciting the donor with the highest energy (bluest donor);
almost negligible residual intensity of all dyes except the last acceptor.

The present invention finds advantageous application in nucleic acid analysis, hystochemistry, cytofluorimetry, patogenic bacteria detection.

These and other object will be disclosed in detail also by means of figures and examples.

In the Figures, a.u. means arbitrary unit.

DETAILED DESCRIPTION OF THE INVENTION

The silica nanoparticle of the present invention are disclosed in WO2010/013136 and WO2010/013137 and can be prepared by processes therein described. All the embodiments, conditions, and teachings disclosed in the above references are applicable also in the present invention.

Figure 7:
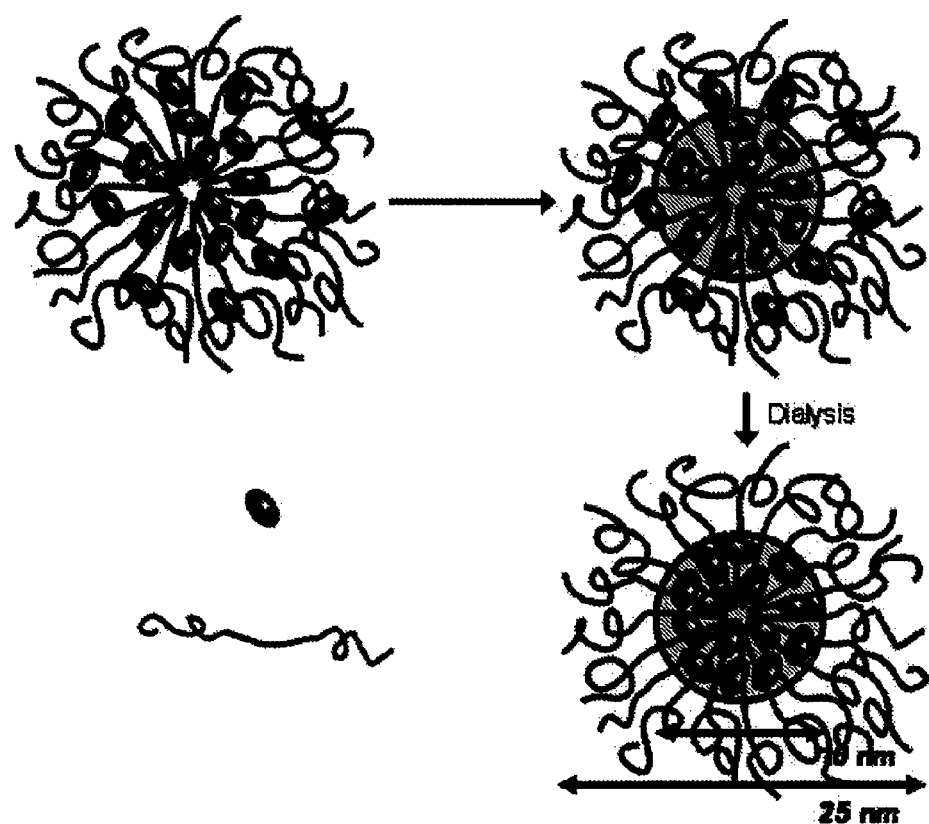
FIG. 7 shows a depiction of an example preparation of silica nanoparticles.

To the purpose of a general understanding of the present invention, there is provided a scheme of preparation of the silica nanoparticles, such as the preparation of silica nanoparticles depicted in FIG. 7.

The fluorophore (dye) is mixed with a surfactant to form a micelle, which is subsequently reacted with an alkoxysilane to form a silica nanoparticle, finally the nanoparticle is isolated. It will be noted that the dye is confined within the nanoparticle silica core.

In a first preferred embodiment of the present invention, core-shell silica-PEG (polyethylene glycol) nanoparticles are prepared adapting previously reported procedures in E. Rampazzo, S. Bonacchi, R. Juris, M. Montalti, D. Genovese, N. Zaccheroni, L. Prodi, D. C. Rambaldi, A. Zattoni, P. Reschiglian *J. Phys. Chem. B*, 2010, 114(45), 14605-14613). Modification of the previous Rampazzo e al. process is necessary in order to confine the dyes in the silica nanoparticle core. In a typical preparation, a suitable amount of surfactant, for example Pluronic F127 and the desired amount of the alkoxysilane derivatized or water insoluble dyes are solubilized in a suitable solvent, such as a halogenated hydrocarbon or an organic one with similar solvent properties, for example dichloromethane. After a homogeneous solution is obtained, the solvent is eliminated, for example by evaporation by means of a inert gas stream and/or under vacuum at a temperature not affecting the stability of the product, such as room temperature. A inert ionic salt (for example NaCl) is added to the solid residue in order to increase ionic strength of the solution and the mixture is solubilized at room temperature with a diluted acidic aqueous solution. This solution can contain a weak acid (for example acetic acid) or a stronger one (for example HCl). A silica precursor, for example TEOS, is then added to the resulting aqueous homogeneous solution followed by a silanizing compound, for example TMSCl, after a sufficient amount of time, for example 3 hours.

After completion of the reaction, within 20-72 hours (for example 48 hours), the nanoparticle is isolated from the reaction mixture. Isolation methods are well-known, in a preferred embodiment, dialysis against water is used.

Moreover, alternative synthetic schemes can be used, especially with dyes not stable in acidic environment. In a typical preparation, the surfactant, for example Pluronic F127, and the desired amount of the alkoxysilane derivatized or water insoluble dye/s is solubilized in dichloromethane. After elimination of the solvent, an inert salt such as NaCl is added to the solid residue and the mixture is subsequently solubilized at room temperature with water. Tetramethylorthosilicate (TMOS) is then added to the resulting aqueous homogeneous solution followed by trimethylsilyl chloride (TMSCl) after a suitable amount of time, for example 15 min. The reaction is carried out at completion for a sufficient time, for example 24-72 hours, preferably 48 hours and the final product is isolated. Dialysis is an example of isolating method.

According to the above mentioned references, the following terms are intended as per the definitions herein provided.

In accordance with the present invention, it is provided a silica nanoparticle comprising a micelle, which in turn has a substantially hydrophilic shell (i.e. a part oriented towards the exterior) and a substantially hydrophobic inner part, which in turn contains a core, located in the area of the inner part of the micelle and comprises a silicate network; and a first and at least a second dye.

By the term "micelle" it is meant either micellar aggregates (comprising molecules of only one kind of surfactants) or micellar co-aggregates (comprising molecules of many kinds of surfactants). According to some embodiments, micelles are micellar aggregates. In particular, the particles are essentially spherical in shape.

By the term "substantially hydrophilic" it is intended a region of the nanoparticle, a molecule or a portion of a molecule, such as a chain that has a water solubility higher than the water solubility of a substantially hydrophobic chain. Advantageously, the substantially hydrophilic part has a higher solubility in water than in ethanol. By the term "substantially hydrophobic" it is intended a region of the nanoparticle, a molecule or a portion of a molecule, such as a chain, that has a water solubility lower than the water solubility of a substantially hydrophilic chain. Advantageously, the substantially hydrophobic part is substantially lipophilic. Substantially lipophilic region of the nanoparticle, molecular portion (or chain or compound) means a region, molecular portion (or chain or compound) that has a higher solubility in ethanol than in water.

By the term "recognition functionality" it is intended a functionality able to bind a specific substrate or analyte. Advantageously, the substrate and/or the analyte is/are a bio-molecule.

By the term "heterogroup" it is intended a substituent that differs from the components of Hydro[1] and Hydro[2] and presents at least one heteroatom and/or at least one unsaturated bond. Heterogroups can function as intermediate groups, that, through a reaction, are substituted with or bind a recognition functionality.

Advantageously, the heterogorup is selected from the group consisting of: —OCO(CH$_2$)$_2$COOH, —SH, —N$_3$, —C≡CH, —SO$_3$Na, —(CH$_2$)$_3$—SO$_3$Na, —SO$_3$CH$_3$, —OPO$_3$H$_2$, —COOH, —OCH$_2$COOH.

By the term "good overlap" it is intended an overlap integral J defined according to the Forster theory that is greater than $1 \times 10^{12}$ M$^{-1}$ cm$^{-1}$ nm$^4$, conveniently greater than $1 \times 10^{14}$ M$^{-1}$ cm$^{-1}$ nm$^4$, These references also disclose generically active compound intended as an organic or metallo-organic one that is emissive and/or electroactive and/or contrast agent and/or able to emit positrons. The emitting compound is defined as a compound able to emit energy, preferably as detectable electromagnetic radiations (luminescent compound) or as heat. The emitting compound can be able to emit by its own and/or in combination with at least a second emitting compound, even through appropriate processes of energy transfer in between luminescent species and the emission can take place through fluorescence, phosphorescence, electrochemiluminescence processed or through chemiluminescence reactions. The emitting compound can be fluorescent or luminescent, the latter is in particular either phosphorescent or electrochemiluminescent.

The present invention specifically refers to a selection of dyes from the ones embodied by the above WO2010/013136 and WO2010/013137, which are dyes with the following properties:
a first and at least a second dye are contained in the core of the above silica nanoparticle; wherein said first and said at least second dye are a dye with the respective relationship of donor-acceptor couple in an energy transfer process and have with a molar absorption $\epsilon \geq 10,000$ M$^{-1}$ cm$^{-1}$ preferably $\geq 30,000$ M$^{-1}$ cm$^{-1}$, more preferably $\geq 100,000$ M$^{-1}$ cm$^{-1}$, for the considered spectral region, a fluorescence quantum yield $\phi \geq 0.01$, preferably $\geq 0.04$, more preferably $\geq 0.30$, a functional group (such as for example amine, —COOH, —N$_3$, alkyne, alkene, acryloyl, —SH, maleimide, aldehyde, —OH, isothiocyanate, sulfonyl chloride, iodoacetyl, TCT (2,4,6-Trichloro-1,3,5-triazine) or an activated carboxylic group such as NHS and NHS-sulfo esters (N-hydroxysuccinimide and sulfo N-hydroxysuccinimide), TFP ester (2,3,5,6-Tetrafluorophenol), PFP ester (pentafluorophenol), HOBt ester (1-hydroxybenzotriazole), N-acylimidazole) suitable for the introduction of a trialkoxysilane moiety, and a good overlap integral, according to the Förster theory, between said donor and said acceptor dye.

According to the present invention, the selected dye is derivatized in order to be covalently linked to the silicate network of the core of said silica nanoparticle or it is lipophilic (insoluble in water) in order to be confined in the central part of the micelles and therefore in the core of said silica nanoparticle.

In a preferred embodiment of the present invention, the dye is linked to a C$_1$-C$_4$ trialkoxy silane, more preferably to a C$_2$ or C$_1$ trialkoxy silane.

The donor dye is a dye emitting at a shorter wavelength with respect to the acceptor dye.

In a first preferred embodiment, the donor dye is a coumarinic dye, or a xanthene derivative dye such as fluorescein or a derivative thereof.

In a more preferred embodiment, the donor coumarinic dye, already linked to a trialkoxysilane, is selected from the group consisting of 7-(diethylamino)-N-(3-(triethoxysilyl)propyl)-2-oxo-2H-chromene-3-carboxamide also named (7-(diethylamino)-N-(3-(triethoxysilyl)propyl)coumarin-3-carboxamide) (DEAC triethoxysilane; in the following of this description also identified as D) and 11-oxo-N-(3-(triethoxysilyl)propyl)-2,3,5,6,7,11-hexahydro-1H-pyrano[2,3-f]pyrido[3,2,1-ij]quinoline-10-carboxamide (coumarin 343 triethoxysilane; in the following of this description also identified as D2).

Preferred acceptor dyes, to be combined with the donor dye are selected from the group consisting of: the bodipy triethoxysilane derivative 2,6-diethyl-4,4-difluoro-1,3,5,7-tetramethyl-8-(4-((3-(triethoxysilyl)propyl)carbamoyl)phenyl)-3a,4a-diaza-4-bora-s-indacene (Bodipy TMDE Ph triethoxysilane; in the following of this description also identified as B), the bodipy triethoxysilane derivative 4,4-difluoro-1,3,5,7-tetramethyl-8-(4-((3-(triethoxysilyl)propyl)carbamoyl)phenyl)-3a,4a-diaza-4-bora-s-indacene] (Bodipy TM-Ph triethoxysilane; in the following of this description also identified as B2), Bodipy TM-Et triethoxysilane (4,□4-difluoro-1,□3,□5,□7-tetramethyl-8-(3-oxo-3-((3-(triethoxy-silyl)-propyl)amino)propyl)-3a,□4a-diaza-4-bora-s-indacene) in the following of this description also identified as B1a Rhodamine B triethoxysilane derivative (in the following of this description also identified as R), the triethoxysilane derivative of cyanine 2-((1E,3E,5E)-5-(1-(6-(2,5-dioxopyrrolidin-1-yloxy)-6-oxohexyl)-3,3-dimethylindolin-2-ylidene)penta-1,3-dienyl)-1-ethyl-3,3-dimethyl-3H-indolium iodide (Chromis 645 C NHS, in the following of this description identified as C5) and the triethoxysilane derivative of 2-((E)-2-((E)-2-(4-(5-(2,5-dioxopyrrolidin-1-yloxy)-5-oxopentanamido)phenoxy)-3-((Z)-2-(3-ethyl-1,1-dimethyl-1H-benzo[e]indol-2(3H)-ylidene)ethylidene)cyclohex-1-enyl)vinyl)-3-ethyl-1,1-dimethyl-1H-benzo[e]indolium iodide (Chromis 800 C NHS), in the following description identified as C7 and the triethoxysilane derivative of Sodium 2-((E)-2-((E)-2-(4-(5-(2,5-dioxopyrrolidin-1-yloxy)-5-oxopentanamido)phenylthio)-3-((Z)-2-(3-ethyl-1,1-dimethyl-6-sulfonato-1H-benzo[e]indol-2(3H)-ylidene)ethylidene)cyclohex-1-enyl)vinyl)-3-ethyl-1,1-dimethyl-1H-benzo[e]indolium-6-sulfonate (Chromis 830A NHS), in the following of this description also identified as C2.

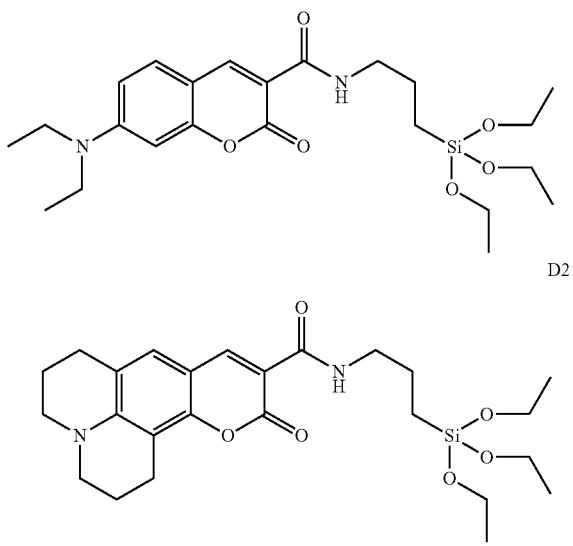

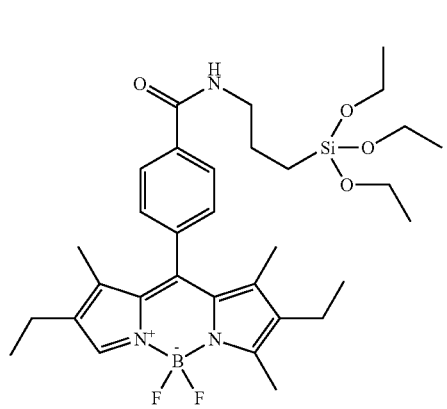

B

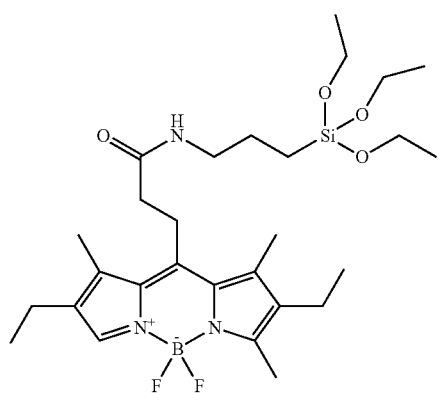

B1

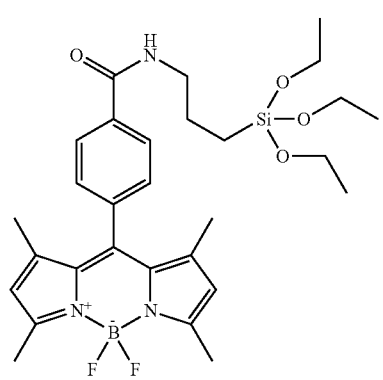

B2

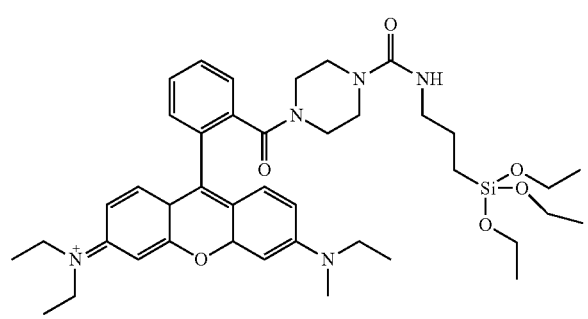

R

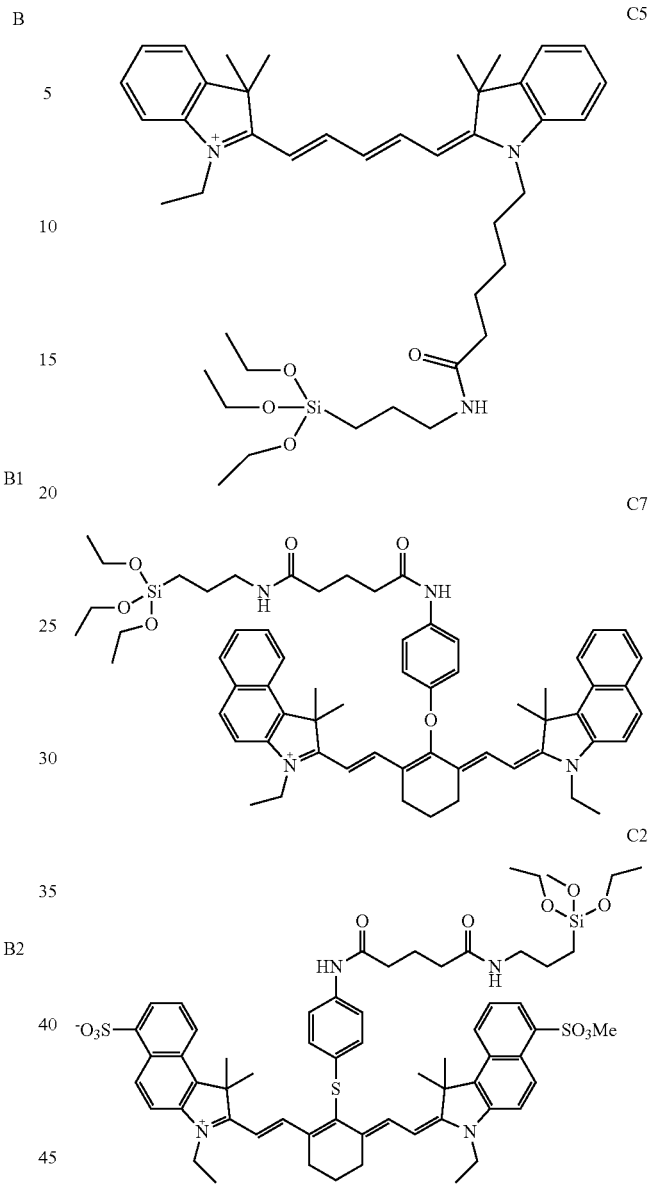

The preferred combinations according to the present invention are:
DB, DR, DC5, DBR, DBC5, DRC5, DBRC5, DBRC5C7; D2B2, D2R, D2C5, D2C5C2, D2B2C5, D2B2C2, D2B2C5C2; D2B2RC5.

In several applications, such as DNA analysis, cytofluorimetry and histochemistry, the number of excitation sources is limited by the experimental hardware setup. For many applications, the laser line at 405 nm is an excitation source which is becoming more and more important; therefore, the availability of compounds absorbing at this wavelength is particularly useful.

In a preferred embodiment of the present invention, there is provided a family of dye-doped silica nanoparticles (DDNs) containing two kind of dyes. This embodiment is also referred to as Nano-Tandem Dye (N-TD) and based on silica nanoparticles doped with two different kind of dyes in which a very efficient energy transfer process between ensures an almost quantitative quenching of the donor and sensitization of the acceptor. As a result, in these nanosystems only the longest-wavelength dye can exhibit significant fluorescence at a short-wavelength excitation. Although many examples of multichromophoric silica nanoparticles featuring energy transfer processes have been reported to date, this feature has not yet been achieved at a satisfactory level (Wang, L.; Tan, W. H. *Nano Letters* 2006, 6, 84; Wang, L.; Zhao, W. J.; O'Donoghue, M. B.; Tan, W. H. *Bioconjugate Chemistry* 2007, 18, 297).

In the context of the embodiment of the present invention relating to the Nano-Tandem Dye, examples of this kind are DEAC as donor (D), and a Bodipy dye as an acceptor, TMDE-Ph-COOH (B) in one case and TM-Ph-COOH (B2) the second one. The dyes were chosen in order to fulfil the following requirements: (i) a high (>40,000 M-1 cm-1) molar absorption coefficient $\epsilon$; (ii) a very high (>0.50) fluorescence quantum yield $\Phi$, (iii) a functional group for an easy introduction of a trialkoxysilane group and (iv) a good overlap integral, according to the Förster theory (Förster, T. *Discuss. Faraday Soc.* 1959, 27, 7) between the a donor and the acceptor.

In another preferred embodiment of the present invention, there is provided a family of dye-doped silica nanoparticles (DDSNs) containing four different dyes: DEAC triethoxysilane (D), the triethoxysilane derivative of Bodipy TMDE-Ph-COOH (B), the Rhodamine B derivative (R), the cyanine Chromis 645 C derivative (C5) in all their possible combinations using in all cases a doping degree of 0.01-1.0%, preferably 0.05-0.5%, for example 0.1% with respect to the mole of TEOS for B, R, and C5 and of 0.01-1.0%, preferably 0.05-0.5%, for example 0.2% with respect to the mole of TEOS for D. A sample of dye-doped silica nanoparticles containing five different dyes D (0.2%), B, R, C5, C7 (0.1%) was also prepared as example of near infrared emitting system. In the case of nanoparticles doped with D alone or with the couple D and B, the nanoparticles were prepared also using for D a doping degree of 0.05, 0.1 and 0.4%. A sample of dye-doped silica nanoparticles containing four different dyes D2 (0.2%), B2, C5, C2 (0.1%) was also prepared to show the generality of the present invention.

The dyes were chosen in order to fulfil the following requirements: (i) a high ($\geq$10,000$M^{-1}$ $cm^{-1}$, preferably $\geq$30,000 $M^{-1}$ $cm^{-1}$, more preferably $\geq$100,000 $M^{-1}$ $cm^{-1}$) molar absorption coefficient $\epsilon$ at least for the considered spectral region, around the maximum absorption of the fluorophore; (ii) a high ($\geq$0.01, preferably $\geq$0.04, more preferably $\geq$0.30) fluorescence quantum yield $\Phi$, (iii) a functional group for an easy introduction of a trialkoxysilane group (or as an alternative an overall insolubility in water) and (iv) a good overlap integral, according to the Förster theory, between the dye D as a donor and B as an acceptor, between B as a donor and R as an acceptor, and between R as a donor C as an acceptor in a cascade way.

To evaluate the effectiveness of this last requirement, we have calculated the Förster radius $R^0$ relative to each pair of dyes belonging to the same series. The values are reported in Table 1; as it can be seen, almost any combination of dyes provides a rather good donor-acceptor couple. Moreover, each dye is a good acceptor towards its own emission, so that also homo-ET processes are actively contributing to the overall photophysics of the nanoparticles.

TABLE 1

Förster radius $R^0$ (Å) for all donor-acceptor couples of the first series. Homo-ET $R^0$ are highlighted with bold character, while the closest couples with *italic* character.

| | | Acceptor | | | |
|---|---|---|---|---|---|
| | | D | B | R | C5 |
| Donor | D | 32.1 | *37.4* | 38.3 | 40.9 |
| | B | — | 46.1 | *57.1* | 55.4 |
| | R | — | — | 47.1 | *60.3* |
| | C5 | — | — | — | 61.4 |

TABLE 2

Förster radius $R^0$ (Å) for all donor-acceptor couples of the second series. Homo-ET $R^0$ are highlighted with bold character, while the closest couples with *italic* character.

| | | Acceptor | | | |
|---|---|---|---|---|---|
| | | D2 | B2 | C1 | C2 |
| Donor | D2 | 26.5 | *36.3* | 40.1 | 32.1 |
| | B2 | — | 42.6 | *46.1* | 38.4 |
| | C5 | — | — | 61.1 | *55.2* |
| | C2 | — | — | — | 45.9 |

Nanoparticles doped with only one kind of dye (reference)

In order to better understand the present invention, the most important parameters of the nanoparticles doped with only one kind of dyes are shown in table 3.

It is to note that a much higher brightness is always observed in the nanoparticles, mainly because of the higher absorption coefficient due to the inclusion of several dyes in each nanostructure. On the other hand, the fluorescence quantum yield is less dramatically affected. In same cases, an increase of this parameter has been observed (B1, C1, and R), most probably because of the higher rigidity of the surrounding environment, while in the other cases the decrease in the fluorescence quantum yield observed upon inclusion of the dye in the nanoparticle core can be attributed to parasite self-quenching processes (Montalti, M.; Prodi, L.; Zaccheroni, N.; Zattoni, A.; Reschiglian, P.; Falini, G. *Langmuir* 2004, 20, 2989). Although further research efforts should be devoted to minimize such effect, it is important to underline again that in all cases such a decrease is more than counterbalanced by the increase of the absorption.

TABLE 3

Main photophysical data of the different dyes in ethanol and inside the silica nanoparticles in water dispersion.

| | | Absorption | | Emission | | | | S-S |
|---|---|---|---|---|---|---|---|---|
| SAMPLE | n° dye/NP | $\lambda$ max (nm) | $\epsilon$ max | $\lambda$ exc (nm) | $\lambda$ max (nm) | $\phi$ absolute | $\tau$ (ns) | (nm) |
| D@NP | 10.5 | 420 | 4.59E+05 | 400 | 460 | 0.4 | 2.6 | 44 |
| D EtOH | — | 392 | 4.37E+04 | 362 | 446 | 0.65 | 2.9 | 54 |
| D2@NP | 11.5 | 432 | 3.70E+05 | 400 | 485 | 0.21 | 3.4 | 53 |

TABLE 3-continued

Main photophysical data of the different dyes in ethanol and inside the silica nanoparticles in water dispersion.

| SAMPLE | n° dye/NP | Absorption | | Emission | | | | S-S |
|---|---|---|---|---|---|---|---|---|
| | | λ max (nm) | ε max | λ exc (nm) | λ max (nm) | φ absolute | τ (ns) | (nm) |
| D2 EtOH | — | 417 | 3.2E+04 | 400 | 475 | 0.71 | 3.5 | 53 |
| B@NP | 7 | 526 | 4.38E+05 | 500 | 538 | 0.85 | 7.6 | 12 |
| B EtOH | — | 523 | 6.26E+04 | 508 | 534 | 0.65 | 5.0 | 11 |
| B2@NP | 7.4 | 500 | 5.40E+05 | 480 | 510 | 0.57 | 5.0 | 11 |
| B2 EtOH | — | 498 | 7.305E+04 | 475 | 504 | 0.87 | 5.7 | 8 |
| R@NP | 10.9 | 570 | 1.09E+06 | 540 | 590 | 0.45 | 3.3 | 19 |
| R EtOH | — | 560 | 1.00E+05 | 534 | 580 | 0.40 | 2.5 | 20 |
| C5@NP | 3.8 | 650 | 7.60E+05 | 610 | 670 | 0.44 | 2.2 | 18 |
| C5 EtOH | — | 645 | 2.00E+05 | 625 | 665 | 0.32 | 1.2 | 19 |
| C2@NP | 6.7 | 842 | 1.68E+06 | 780 | 867 | 0.02 | —* | 25 |
| C2 EtOH | — | 833 | 2.25E+05 | 770 | 855 | 0.03 | —* | 27 |
| C7@NP | 3.4 | 835 | 6.80E+05 | 760 | 860 | 0.11 | 0.5 | ? |
| C7 EtOH | — | 823 | 2.00E+05 | 760 | 850 | 0.08 | 0.4 | ? |

NP: nanoparticle in water
EtOH: indicated dye in ethanol
S-S: Stokes shift
*experimental setup unsuitable for lifetimes determination in the NIR spectral range If the case of B, R, C5 and C7 the photophysical data of the different dyes in the nanoparticles are very similar to the ones shown by the single dyes in absolute ethanol, as expected because of the π-π* nature of the transition involved, with very small red shifts (<10 nm) both in the absorption and in the emission spectra and some lengthening of the excited state lifetime. This effect is most probably due to the protection offered by the rigid silica matrix, an effect that is more evident in the case of C5, whose non-radiative deactivation is mainly due to the trans-cis photo-isomerization. It is also interesting to note that in the case of B and C5, a change in the doping degree of the nanoparticles does not induce noticeable changes in the excited state lifetime and in the fluorescence quantum yield, indicating that self-quenching mechanisms are for these dyes almost inefficient. On the contrary, these processes should not be excluded in the case of R, for which a not negligible reduction of the fluorescence quantum yield upon increasing the doping degree can be observed. In the case of D, its inclusion in the silica matrix induces a much more pronounced red-shift, as expected because its lowest excited state has a charge-transfer character. Because of the nature of the excited state, this dye shows also the largest Stokes-shift. From the data reported in Table 4, it is clear that in the case of the coumarin dye the self-quenching processes are quite efficient when more than 5 molecules of dye per nanoparticles are present, i.e., when the mean distance among the dye is shorter than 6.5 nm. In general, the brightness(es) of the nanoparticles is (are) higher respect to the ones of the single dye, and can be further increased increasing the doping degree when self quenching processes are not very efficient (as in the case of R) or, better, when they are negligible (as in the case of B and C5).

TABLE 4

Photophysical properties of DDSN doped with a different amount of D, B and B2

| SAMPLE[a] | n° dye/NP | φ absolute | τ (ns) |
|---|---|---|---|
| $D_{0.05}$ | 2.2 | 0.63 | 2.8 |
| $D_{0.1}$ | 5.2 | 0.58 | 2.7 |
| $D_{0.2}$ | 10.5 | 0.4 | 2.2 |

TABLE 4-continued

Photophysical properties of DDSN doped with a different amount of D, B and B2

| SAMPLE[a] | n° dye/NP | φ absolute | τ (ns) |
|---|---|---|---|
| $D_{0.4}$ | 21.3 | 0.29 | 1.9 |
| $B_{0.1}$ | 7.0 | 0.85 | 7.2 |
| $B2_{0.1}$ | 5.3 | 0.66 | 6.8 |
| $B2_{0.2}$ | 10.4 | 0.53 | 6.4 |

[a]subscripts correspond to the nanoparticles doping levels (mol dye vs mol TEOS)

Multichromophoric Nanoparticles.

In one embodiment of the present invention, the nanoparticles comprise couples of two dyes.

In another embodiment of the present invention, the nanoparticles comprise three dyes.

In still another embodiment of the present invention, the nanoparticles comprise four dyes, In a further embodiment of the present invention, the nanoparticles comprise five dyes, The efficiency of energy transfer (ET) processes $\eta_{ET}$ between the donor and the acceptor in each set of nanoparticles has been evaluated on the basis of the quenching of the fluorescence of the donor according to eq. 1, where $I_D$ and $I°_D$ are the fluorescence intensity of the donor in the nanoparticles in the presence and in the absence of the acceptor, respectively.

$$\eta_{ET}=(1-I_D/I°_D) \quad (eq\ 1)$$

The data obtained according to eq 1 were always coincident within the experimental errors with those estimated examining the sensitization of the fluorescence of the acceptor, suggesting that other deactivation processes from the donor to the acceptor were negligible. Because of the high efficiency of the ET process, for all the nanoparticles studied the excitation spectra were very similar to the absorption ones. In the exemplary case of nanoparticles containing D, B and B1, we investigated in particular the effect on the photophysical properties of the number of donor molecules per nanoparticle. This approach could seem, at a first glance, not very appropriate, since it has not been conceived to obtain, as the only interesting feature, the highest possible efficiency for the energy transfer process. This goal, in fact, could be reached in a more effective way increasing the concentration of the acceptor inside the nanoparticle, since the mean distance among a donor in its excited state and an acceptor changes only if the concentration of this latter unit changes. As a consequence, in the absence of other processes, only the concentration of the acceptor should have an effect on the efficiency of hetero-energy transfer. However, to have large Stokes shifts and the possibility of single wavelength excitation, excitation is to be performed on the donor and, from an analytical point of view, the increase of the number of acceptor molecules does not lead to a significant increase in the brightness, while the increase of the number of donor molecules does.

As it can be seen in Table 5, the rate constant for the energy transfer process, calculated according to eq. 2, (where $\tau^°$ is the excited state lifetime of the donor in the absence of the acceptor), does not change significantly upon changing the concentration of the donor.

$$k_{ET}=1/[\tau^°(1/\eta_{ET}-1)] \qquad (eq\ 2)$$

Figure 1:
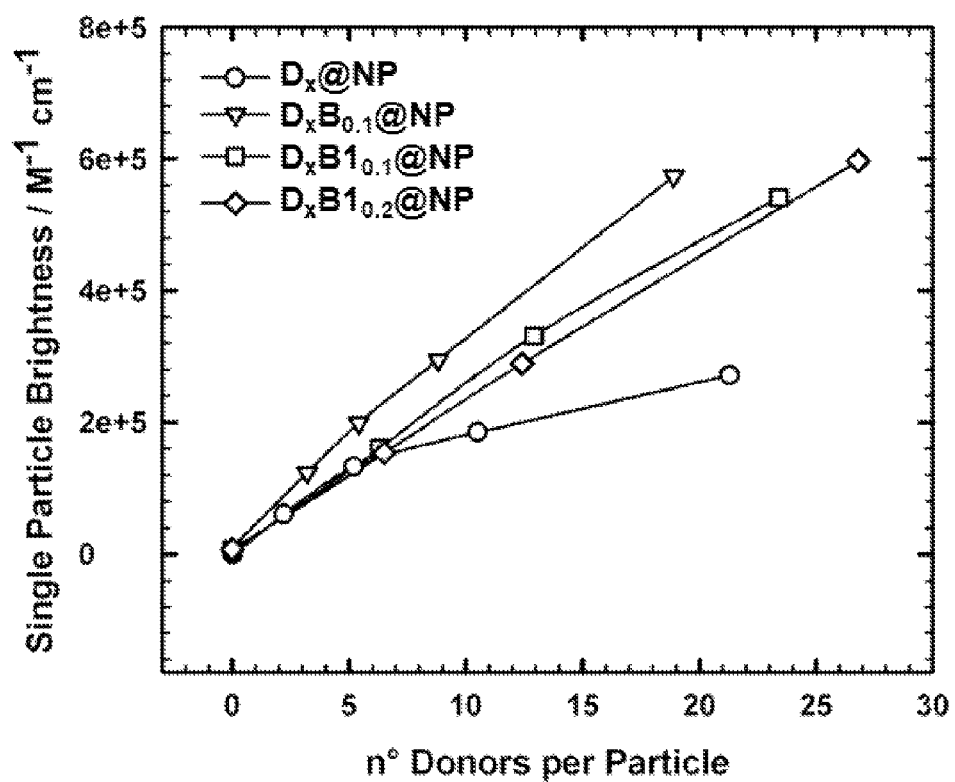
FIG. 1 shows brightness level of the nanoparticle containing $D_x$ (circles), the couple $D_x$-$B_{0.1}$ (triangles), the couple $D_xB1_{0.1}$ (squares) and of the couple $D_xB1_{0.2}$ (rhombus) as a function of the increasing number of molecules of D per nanoparticle (see table 5, $\lambda_{ex}$=400 nm). Here, x=(moles of the dye/moles of TEOS)*100.

However, it is to note that the introduction of the energy transfer process offers a very competitive pathway to the parasite self-quenching process observed for D, with the consequence that the efficiency of the energy transfer remains relatively high (>85%) also for high doping degrees. This result leads to an important advantage from an analytical point of view, i.e., the brightness of the system looking at the emission of the bodipy B or B1 but exciting the coumarin D (the experimental conditions for which these nanoparticles have been conceived) undergoes a five-fold increase upon increasing the doping degree of D from 0.05 to 0.4%, so that a parallel increase of the signal can be achieved, an effect that can not be observed when only D is present (see also FIG. 1). This result, that to our knowledge has not yet been reported in the literature so far, is important for the design of new nanoparticles, since suggests a possible way to use dyes that, as fluorescein, are known to suffer from self-quenching phenomena.

The Tandem Dye nanoparticle provided by the present invention, here shown in the exemplary embodiments of $D_xB_y$@NP, or $D_xB1_y$@NP, where X and Y represent the mol of dye D, B and B1 vs mol of TEOS respectively represents a family of two fluorescent labels that can be both efficiently excited at 405 nm (emission wavelength of a laser source typically employed in cytofluorimetry), a high brightness with two distinguishable emission bands and almost no cross-interference. All these results make these kind of core shell nanoparticles very interesting as labels for fluorescence-base analytical techniques.

Additional interesting phenomena occurring in this confined media, are homo-energy transfer processes that allow energy migration inside the nanoparticle. The occurrence of these processes is confirmed by the lower values of anisotropy observed for increasingly doped NPs. When embedded in the silica matrix the rotational freedom of the dye is strongly reduced, so that the only possible mechanism for fluorescence depolarization is homo-energy transfer, which is more likely to occur the closer are the dyes, i.e. at high doping ratios. This effect is higher for B, B1, R and C5, as expected because the Stokes shift is smaller and the overlap integral consequently higher. However, also for D this effect is not negligible, especially when the number of molecules is high: the reduction of the anisotropy value measured despite a shortening of the excited state lifetime (that usually induces the opposite effect) is a clear indication of the occurrence of this process (Table 7). As it can be seen from the table 6, when three or four dyes are inserted in the core of the nanoparticles, the efficiency of the quenching of the different donors and the sensitization of the acceptors are even more pronounced. In particular, the residual intensity of the different donors rarely exceeds the value of 5%. It is particularly important to underline that the efficiency observed in this family of nanoparticles is unexpectedly higher to the ones reported so far for other multichromophoric silica nanoparticles. Although the present inventors do not wish to bound by any theory, a possible explanation to this unexpected increase relies on the different structure of the nanoparticles. In general, the former examples were based on nanoparticles prepared according to the Stöber methodology as modified by van Blaaderen, with a diameter typically exceeding 50 nm. We had already demonstrated (E. Rampazzo, S. Bonacchi, M. Montalti, L. Prodi, N. Zaccheroni, J. Am. Chem. Soc., 2009, 129, 14251-14256) that this synthetic strategy leads spontaneously to a core/shell structure, where the concentration of the dye is high in the core but much lower in the outer shells. The low density (implying a larger interchromophoric distance) presumably limits the efficiency of the energy transfer of the dyes buried in these outer layers. Our synthetic methodology, on the contrary, leads instead to NPs that are more homogeneous, both because the NPs are smaller and because the formation of the NPs occurs in confined nanoreactors, and this can account for the unprecedented efficiency we have observed.

As it can be seen from the table 6, when three or four dyes are inserted in the core of the nanoparticles, the efficiency of the quenching of the different donors and the sensitization of the acceptors are even more pronounced.

TABLE 5

Photophysical properties of DDNS samples doped with D, B and B1.

| Samples[a] | <dye/NP> (donor) | <dye/NP> (acceptor) | $\epsilon(\lambda_{max})$ (M$^{-1}$ cm$^{-1}$)(nm) Donor | $\epsilon(\lambda_{max})$ (M$^{-1}$ cm$^{-1}$)(nm) Acceptor | $\phi^b$ Donor | $\phi^b$ Acceptor | $<\tau>$ (ns) Donor | $<\tau>$ (ns) Acceptor | $\eta_{et}$ | Brightness (M$^{-1}$ cm$^{-1}$) Donor |
|---|---|---|---|---|---|---|---|---|---|---|
| $D_{0.05}$@NP | 2.2 | — | 96800(420) | — | 0.63 | — | 2.8 | — | — | 61000 |
| $D_{0.10}$@NP | 5.2 | — | 228800(420) | — | 0.58 | — | 2.7 | — | — | 133000 |
| $D_{0.20}$@NP | 10.5 | — | 459000(420) | — | 0.40 | — | 2.2 | — | — | 184000 |
| $D_{0.40}$@NP | 21.3 | — | 924000(420) | — | 0.29 | — | 1.9 | — | — | 268000 |
| $B_{0.1}$@NP | — | 7.0 | — | 438000(526) | — | 0.85 | — | 7.2 | — | 372000 |
| $B1_{(0.1)}$@NP | — | 5.3 | — | 392000(524) | — | 0.66 | — | 6.8 | — | 259000 |
| $B1_{(0.2)}$@NP | — | 10.4 | — | 770000(524) | — | 0.53 | — | 6.4 | — | 408000 |
| $D_{0.05}B_{0.1}$@NP | 3.2 | 8.9 | 154000(420) | 557000(526) | 0.063 | 0.88 | 1.1 | 7.2 | 0.90 | 122000 |
| $D_{0.10}B_{0.1}$@NP | 5.4 | 8.2 | 249000(420) | 513000(526) | 0.052 | 0.87 | 1.0 | 7.4 | 0.91 | 197000 |
| $D_{0.20}B_{0.1}$@NP | 8.8 | 7.6 | 397000(420) | 476000(526) | 0.052 | 0.85 | 0.9 | 7.5 | 0.87 | 294000 |
| $D_{0.40}B_{0.1}$@NP | 18.8 | 8.6 | 840000(420) | 538000(526) | 0.041 | 0.79 | 0.7 | 7.7 | 0.86 | 571000 |

TABLE 5-continued

Photophysical properties of DDNS samples doped with D, B and B1.

| Samples[a] | <dye/NP> (donor) | <dye/NP> (acceptor) | $\epsilon(\lambda_{max})$ (M$^{-1}$ cm$^{-1}$)(nm) Donor | $\epsilon(\lambda_{max})$ (M$^{-1}$ cm$^{-1}$)(nm) Acceptor | $\phi^b$ Donor | $\phi^b$ Acceptor | <$\tau$> (ns) Donor | <$\tau$> (ns) Acceptor | $\eta_{et}$ | Brightness (M$^{-1}$ cm$^{-1}$) Donor |
|---|---|---|---|---|---|---|---|---|---|---|
| D$_{0.10}$B1$_{0.1}$@NP | 6.3 | 6.4 | 286000(420) | 474000(524) | 0.099 | 0.66 | 1.2 | 7.1 | 0.85 | 158000 |
| D$_{0.20}$B1$_{0.1}$@NP | 12.9 | 6.1 | 577000(420) | 451000(524) | 0.086 | 0.64 | 1.0 | 7.3 | 0.87 | 326000 |
| D$_{0.40}$B1$_{0.1}$@NP | 23.4 | 6.0 | 1038000(420) | 444000(524) | 0.139 | 0.63 | 0.9 | 7.6 | 0.79 | 541000 |
| D$_{0.10}$B1$_{0.2}$@NP | 6.5 | 11.8 | 301600(420) | 873000(524) | 0.0212 | 0.53 | 0.7 | 6.7 | 0.96 | 153000 |
| D$_{0.20}$B1$_{0.2}$@NP | 12.4 | 11.4 | 562000(420) | 844000(524) | 0.156 | 0.51 | 0.6 | 6.7 | 0.97 | 289000 |
| D$_{0.40}$B1$_{0.2}$@NP | 26.8 | 13.0 | 1198000(420) | 960000(524) | 0.0320 | 0.50 | 0.6 | 6.9 | 0.94 | 597000 |

[a]subscripts correspond to the nanoparticles doping levels (mol dye vs mol TEOS);
[b]quantum yield of acceptor B, B1 and of donor D in the nanoparticles samples.

TABLE 6

Structural and photophysical DDSN doped with the different dyes

| NP sample | eff quenching (%) D | eff quenching (%) B | eff quenching (%) R | eff quenching (%) C5 | IA/ID[a] D | IA/ID[a] B | IA/ID[a] R | IA/ID[a] C5 | Brightness acceptor[b]/1E+5 exc D | Brightness acceptor[b]/1E+5 exc B | Brightness acceptor[b]/1E+5 exc R | Brightness acceptor[b]/1E+5 exc C | $\epsilon$ (NP)[c]/1E+5 |
|---|---|---|---|---|---|---|---|---|---|---|---|---|---|
| D | — | — | — | — | — | — | — | — | 1.47 | — | — | — | 4.59 |
| B | — | — | — | — | — | — | — | — | — | 2.98 | — | — | 4.38 |
| R | — | — | — | — | — | — | — | — | — | — | 3.92 | — | 10.9 |
| C5 | — | — | — | — | — | — | — | — | — | — | — | 2.68 | 7.60 |
| DB | 0.87 | — | — | — | 24.43 | — | — | — | 2.36 | 3.23 | — | — | 3.97 |
| DR | 0.90 | — | — | — | 5.5 | — | — | — | 1.21 | — | 1.37 | — | 5.85 |
| DC5 | 0.89 | — | — | — | 3.6 | — | — | — | 0.67 | — | — | 1.74 | 4.45 |
| BR | — | 0.98 | — | — | — | 17.5 | — | — | — | 2.79 | 2.87 | — | 6.62 |
| BC5 | — | 0.97 | — | — | — | 12.75 | — | — | — | 1.75 | — | 2.96 | 5.22 |
| RC5 | — | — | 0.86 | — | — | — | 4.32 | — | — | — | 2.46 | 2.90 | 9.46 |
| DBR | 0.96 | 0.98 | — | — | 36.79 | 26.05 | — | — | 1.47 | 2.64 | 2.94 | — | 5.32 |
| DBC5 | 0.96 | 0.94 | — | — | 20.24 | — | 8.17 | — | 1.13 | 1.65 | — | 2.94 | 3.61 |
| DRC5 | 0.97 | — | 0.99 | — | 13.5 | — | 28 | — | 0.57 | — | 0.79 | 2.23 | 3.25 |
| BRC5 | — | 0.99 | 0.87 | — | — | 74.33 | 10.83 | — | — | 2.25 | 2.66 | 2.76 | 7.48 |
| DBRC5 | 0.97 | 0.99 | 0.95 | — | 52.83 | 79.43 | 18.7 | — | 1.02 | 2.15 | 2.53 | 2.88 | 2.86 |
| DBRC5C7 | 0.98 | 0.99 | 0.97 | 0.96 | 5.9 | 9.6 | 2.2 | 1.4 | 0.20 | 0.36 | 0.43 | 0.47 | 3.44 |
| | D2 | B2 | R | C5 | | | | | | | | | |
| D2B2C5C2 | 95 | 100 | 99 | 99 | | | | | | | | | |

| NP sample | n° dye/NP D | n° dye/NP B | n° dye/NP R | n° dye/NP C5 | n° dye/NP C7 | $\phi A$[d] | S-S[e] |
|---|---|---|---|---|---|---|---|
| D | 10.5 | — | — | — | — | 0.40 | 44 |
| B | — | 7 | — | — | — | 0.85 | 12 |
| R | — | — | 10.9 | — | — | 0.45 | 19 |
| C5 | — | — | — | 3.8 | — | 0.44 | 18 |
| DB | 8.8 | 7.6 | — | — | — | 0.85 | 121 |
| DR | 13.4 | — | 5.9 | — | — | 0.23 | 170 |
| DC5 | 10.2 | — | — | 5.1 | — | 0.17 | 251 |
| BR | — | 10.5 | 6.7 | — | — | 0.43 | 64 |
| BC5 | — | 7.9 | — | 4.3 | — | 0.43 | 142 |
| RC5 | — | — | 8.2 | 4.9 | — | 0.37 | 101 |
| DBR | 11.3 | 9.3 | 10.2 | — | — | 0.36 | 170 |
| DBC5 | 7.3 | 7.7 | — | 4.3 | — | 0.43 | 253 |
| DRC5 | 7.4 | — | 4.4 | 6.2 | — | 0.18 | 251 |
| BRC5 | — | 7.3 | 7.9 | 4.2 | — | 0.41 | 142 |
| DBRC5 | 5.4 | 5.7 | 6.2 | 3.9 | — | 0.37 | 251 |
| DBRC5C7 | 5.4 | 5.7 | 6.2 | 3.9 | 3.9 | 0.06 | 440 |
| D2B2C5C2 | | | | | | | 435 |

[a]Intensity ratio between acceptor and donor emissions
[b]Nanoparticle brightness, as observed on the last acceptor's emission when excited at the maximum absorption wavelengths of the different donors
[c]Nanoparticle molar extinction coefficient at the wavelength of the first donor's absorbance maximum
[d]Quantum yield of the last energy acceptor
[e]Stokes shift, expressed in nanometers

TABLE 7

Anisotropy data and efficiency of energy transfer for the DB nanoparticles

| NP samples[a] | anis D[b] (~470 nm) | anis B[c] (~550 nm) | τ (nm) | <η sperim> |
|---|---|---|---|---|
| $D_{0.05}$@NP | 0.22 | — | 2.8 | — |
| $D_{0.1}$@NP | 0.17 | — | 2.7 | — |
| $D_{0.2}$@NP | 0.10 | — | 2.2 | — |
| $D_{0.4}$@NP | 0.07 | — | 1.9 | — |
| $D_{0.05}B_{0.1}$@NP | 0.32 | 0.02 | 1.1 | 0.90 |
| $D_{0.1}B_{0.1}$@NP | 0.24 | 0.01 | 1.0 | 0.91 |
| $D_{0.2}B_{0.1}$@NP | 0.20 | 0.00 | 0.9 | 0.87 |
| $D_{0.4}B_{0.1}$@NP | 0.16 | 0.01 | 0.7 | 0.86 |

[a]subscripts correspond to the nanoparticles doping levels (mol dye vs mol TEOS)
[b]upon direct excitation of dye D ($\lambda_{ex}$ = 400 nm).
[c]upon direct excitation of dye B ($\lambda_{ex}$ = 500 nm), Anis $B_{0.1}$@NP = 0.07.

The unprecedented efficiency of the different ET processes in the bi-, tri- or tetra-chromophoric nanoparticles leads, from one side, to a very high overall sensitization, and, from the other side, to a very low residual emission of the different donors.

This material, at the end, presents a very large Stokes shift (up to 440 nm, a value that can be reached using NIR dyes as final acceptors), a very high brightness, even exciting the "bluest" donor, and an almost negligible residual intensity of all the dyes but the last acceptor. All this features, taken together, make these systems very promising for multiplexing, also without separation, since upon single excitation it is possible to obtain the emission colours of the final acceptor, just with a proper choice of the doping dyes. In addition, these nanoparticles appears as valuable solutions for all the diagnostic techniques requiring high brightness associated with large Stokes shift.

It is here underlined one further important advantage provided by the present invention and represented by the Stokes shift of these nanoparticles that is, in the systems here described, larger than 80 nm, a value that allows an efficient reduction of interferences coming from the Rayleigh-Thyndall and Raman bands.

Figure 4:
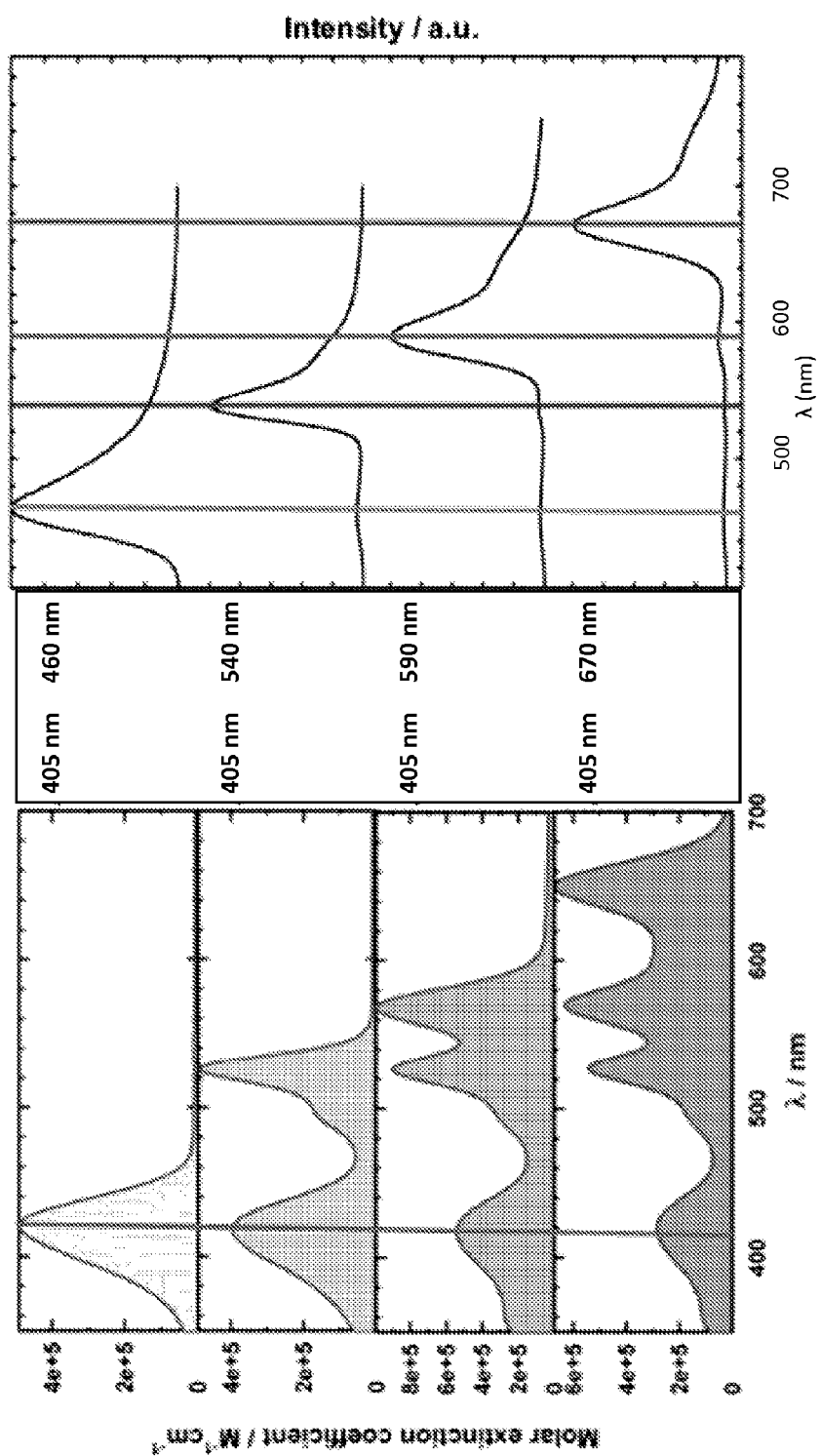
FIG. 4 represents a set of four NPs that present a very high absorption coefficient at 405 nm (emission wavelength of a laser source typically employed in cytofluorimetry), high brightness with four distinguishable emission bands and almost no cross-interference.

From an applicative point of view, because of the observed ET high efficiency, these nanoparticles can be seen as a very effective and reproducible complex tandem dyes. As it can be observed from FIG. 4, D@NP, (D+B)@NP, (D+B+R)@NP, and (D+B+R+C5)@NP represent a set of four NPs that present a very high absorption coefficient at 405 nm (emission wavelength of a laser source typically employed in cytofluorimetry), high brightness with four distinguishable emission bands and almost no cross-interference.

Figure 5:
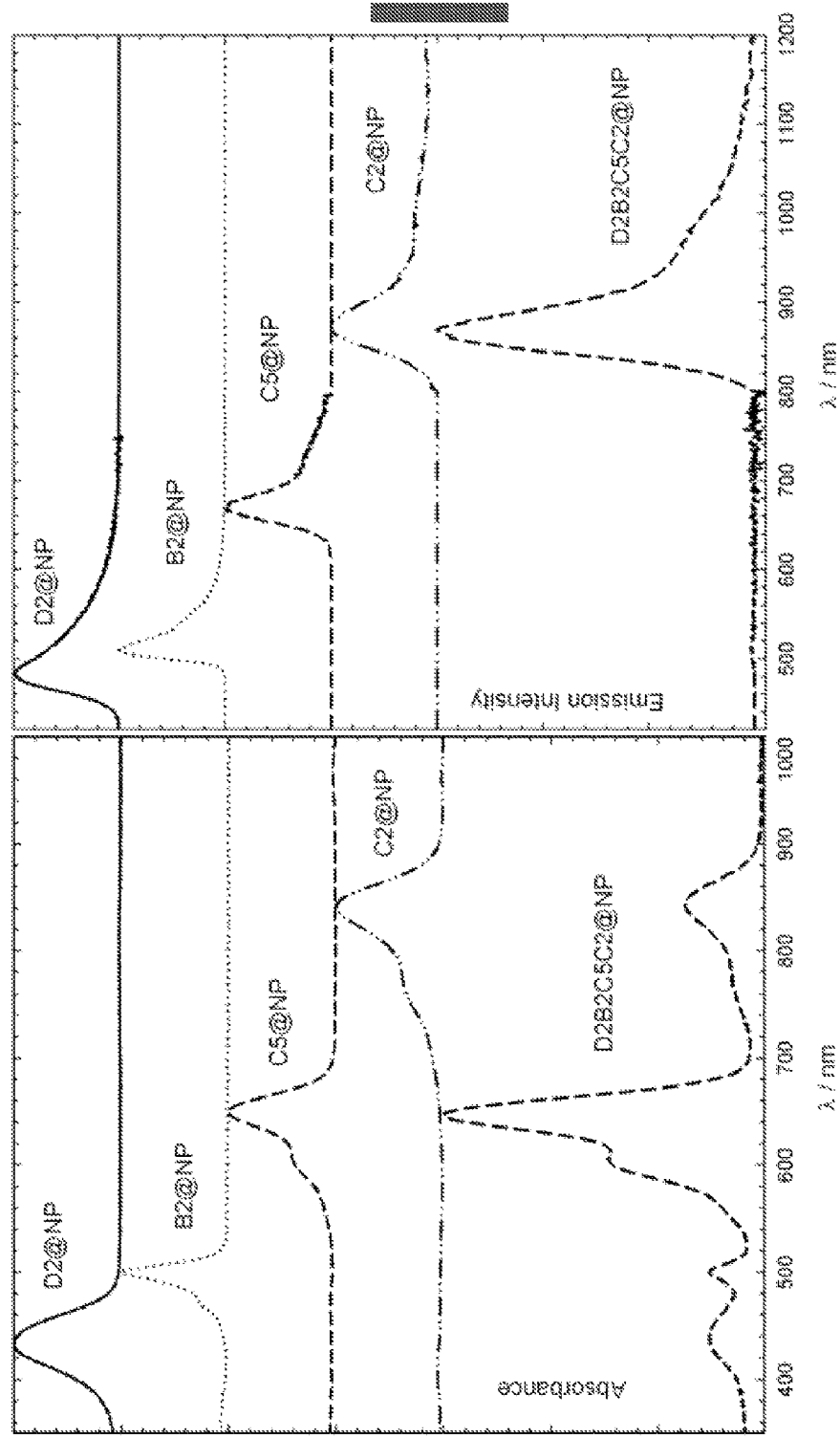
FIG. 5 shows the results obtained with a tetratandem system, whose emission in all the visible range is almost negligible compared to that one of the nanoparticles doped with the single dyes.

Similar, if not better, results could be obtained with the (D2B2C5C2)@NP, whose emission in all the visible range is almost negligible compared to that one of the nanoparticles doped with the single dyes (FIG. 5). It is worth noticing that the difference among the emission wavelength of the lower energy acceptor and the absorption wavelength (pseudo Stokes-Shift) is in this system 435 nm (Table 6), one of the most larger reported so far in the literature.

To prove the almost absence of cross interferences, we adsorbed four samples of glass fibres with D@NP, (DB)@NP, (DBR)@NP, and (DBRC5)@NP respectively.

Figure 6:
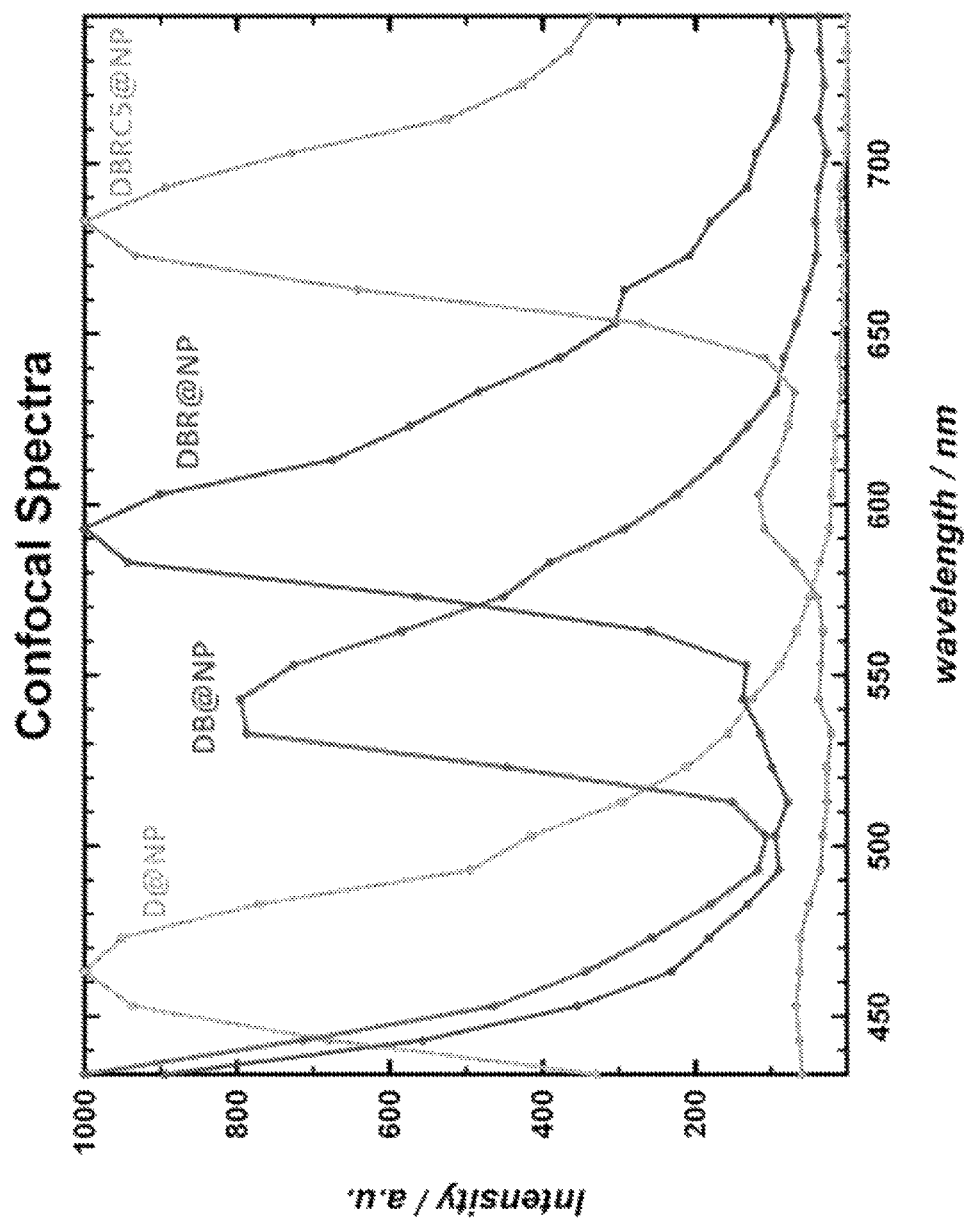
FIG. 6 shows the confocal emission spectra of four sets of glass fibres, where representative nanoparticles of the present invention have been absorbed. The fibres are excited at the same wavelength (405 nm) and are clearly distinguishable.

It can be seen from FIG. 6, the four sets of fibres, all excited at the same wavelength (405 nm), have clearly distinguishable confocal emission spectra, proving the fact that this strategy can lead to the preparation of highly luminescent labels that can surpass in efficiency and versatility the commercial Tandem dyes, that are in any case limited to the binding of two only fluorochromes.

The following examples further illustrate the invention.
Chemicals:

All reagents and solvents were used as received without further purification: non ionic surfactant Pluronic® F127, tetraethyl orthosilicate (TEOS, 99.99%), tetramethyl orthosilicate (TMOS, >99%), chlorotrimethylsilane (TMSCl, ≥98%), hydrochloric acid (fuming, ≥37%), 3-ethyl-2,4-dimethylpyrrole (97%), 4-(chlorocarbonyl)benzoate (≥95%), boron trifluoride diethyl etherate ($BF_3 \cdot Et_2O$), N,N-diisopropylethylamine (DIPEA, ≥99%) and acetic acid (≥99.7%) were purchased from Aldrich. Triethylamine (≥99.5%), 1-hydroxybenzotriazole hydrate (HOBt≥99.0%), N-(3-dimethylaminopropyl)-N-ethylcarbodiimide hydrochloride (EDC.HCl, ≥98.0%), (3-aminopropyl)triethoxysilane (APTES, ≥98.0%), $LiOH \cdot H_2O$ (≥99%), reagent grade dichloromethane, cyclohexane, ethyl acetate and NaCl were purchased from Fluka. 7-(diethylamino)coumarin-3-carboxylic acid (DEAC, ≥98.0%) was purchased from Sigma. Chromis 645 C NHS ((2-((1E,3E,5E)-5-(1-(6-(2,5-dioxopyrrolidin-1-yloxy)-6-oxohexyl)-3,3-dimethylindolin-2-ylidene)penta-1,3-dienyl)-1-ethyl-3,3-dimethyl-3H-indolium iodide)), Chromis 800 C NHS (2-((E)-2-((E)-2-(4-(5-(2,5-dioxopyrrolidin-1-yloxy)-5-oxopentanamido) phenoxy)-3-((Z)-2-(3-ethyl-1,1-dimethyl-1H-benzo[e] indol-2(3H)-ylidene)ethylidene)cyclohex-1-enyl)vinyl)-3-ethyl-1,1-dimethyl-1H-benzo[e]indolium iodide), and Chromis 830A NHS (Sodium 2-((E)-2-((E)-2-(4-(5-(2,5-dioxopyrrolidin-1-yloxy)-5-oxopentanamido)phenylthio)-3-((Z)-2-(3-ethyl-1,1-dimethyl-6-sulfonato-1H-benzo[e]indol-2(3H)-ylidene)ethylidene)cyclohex-1-enyl)vinyl)-3-ethyl-1,1-dimethyl-1H-benzo[e]indolium-6-sulfonate) were purchased from Cyanagen s.r.l. (Bologna-Italy).

A Milli-Q Millipore system was used for the purification of water (resistivity ≥18 MΩ).
Ultrafiltration and Dialysis Experiments:

Nanoparticles ultrafiltration was carried out under nitrogen pressure in a 75 mL stainless steel-glass solvent-resistant stirred cell purchased from Millipore (47 mm filters). The ultrafiltration experimental setup included an Amicon regenerated cellulose membranes (10 kDa cut-off) and an auxiliary reservoir (800 mL) equipped with a concentration selector valve.

Dialysis was performed vs. water at room temperature under gentle stirring with regenerated cellulose dialysis tubing (Sigma, mol wt. cut-off >12000 Da, avg. diameter 33 mm). Filtration of particles solutions was made when necessary using Millipore Durapore filters (0.22, 0.45 μm).

Example 1

Triethoxysilane Derivative of Chromis 645 C NHS, C5

Scheme 1: APTES, dichloromethane

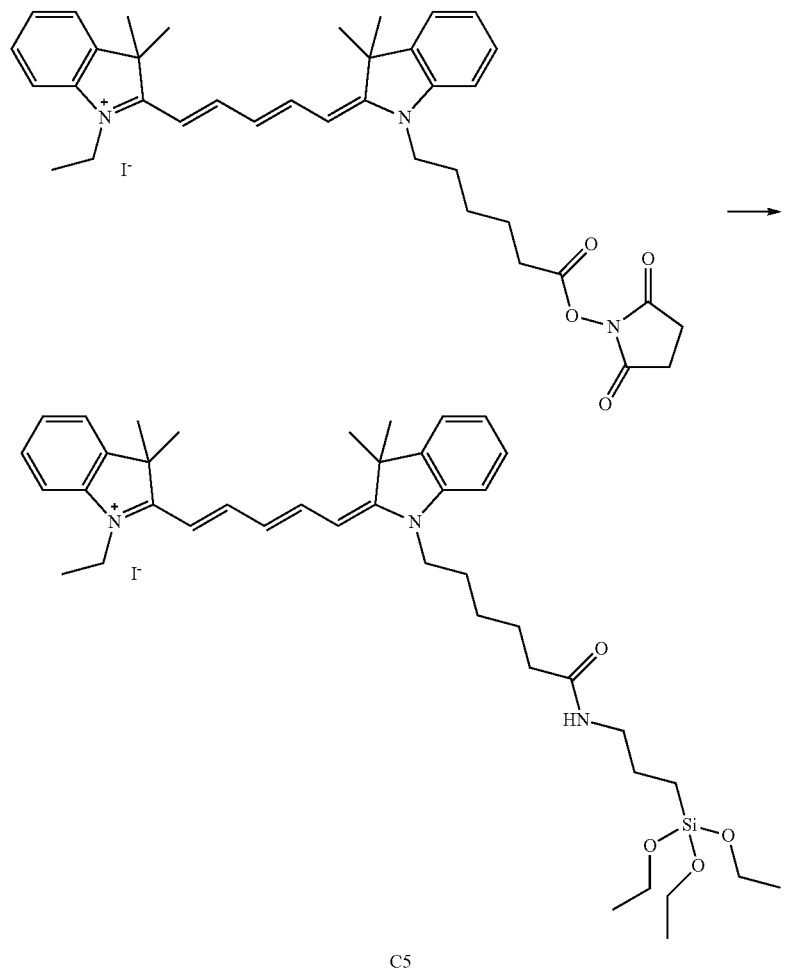

C5

In a glass vial 0.57 mg of Chromis 645 C NHS (0.0008 mmol, 1 eq.) were solubilised with 245 μL of dry dichloromethane. To this solution were added 3.8 μL of a 1:10 (v/v) solution of APTES in dichloromethane (0.0016 mmol, 2 eq.). The mixture was stirred overnight and then used without further purification.

Example 2

Bodipy TM-Ph-COOMe (4,4-difluoro-8-(4-(methoxycarbonyl)phenyl)-1,3,5,7-tetramethyl-3a,4a-diaza-4-bora-s-indacene)

Scheme 2:

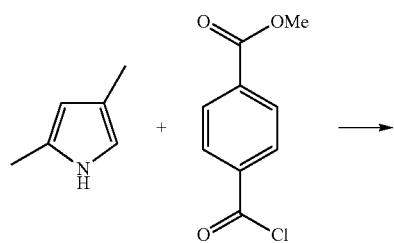

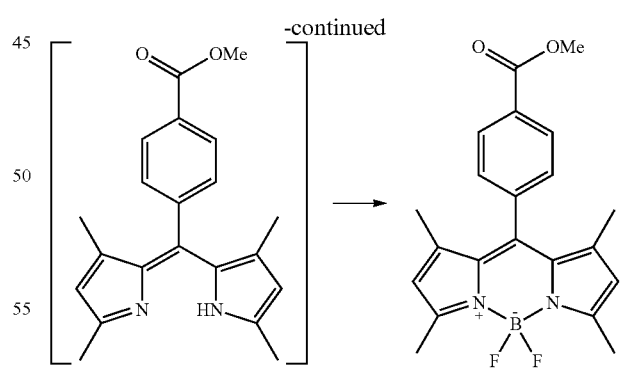

(a) reflux; (b) DIPEA, BF$_3$·Et$_2$O, reflux; (c) purification by silica flash chromatography (cyclohexane/diethyl ether gradient 95:5-9:1-8:2, v/v)

Under a nitrogen atmosphere, in a 3-necked flask equipped with a condenser and a dropping funnel, 460 μL (4.33 mmol, 2 eq.) of 2,4-dimethylpyrrole and 579 mg (4.76 mmol, 2.2 eq.) of magnesium sulfate were dissolved in 6 mL of dichloromethane. To this solution, 498 mg (2.38 mmol, 1.1 eq.) of methyl 4-(chlorocarbonyl)benzoate, solubilized in 4 mL of dichloromethane, were added drop wise over 30 minutes. The reaction mixture was heated to reflux for 3 hours, during which it assumed a deep purple colour, and then cooled at room temperature. Then 1.69 mL (9.53 mmol, 4.4 eq.) of N,N-diisopropylethylamine and—after 15 minutes—1.76 mL (14.3 mmol, 6.6 eq.) of boron trifluoride diethyl etherate were added. The reaction mixture was again heated to reflux for 3 hours, during which fluorescence appeared.

Finally, the solution was diluted with water and extracted two times with dichloromethane; the combined organic phases were dried on sodium sulfate and evaporated under reduced pressure. The resulting mixture was purified by means of flash chromatography on silica gel using a cyclohexane/ether gradient (95:5-9:1-8:2, v/v) as eluent, affording 215 mg of an orange solid (yield 26%).

$^1$H NMR (CDCl$_3$, 200 MHz, 25° C.) δ: 8.19 (d, J=8 Hz, 2H), 7.41 (d, J=8 Hz, 2H), 6.00 (s, 2H), 3.98 (s, 3H), 2.57 (s, 6H), 1.37 (s, 6H).

Example 3

Bodipy TM-Ph-COOH (8-(4-carboxyphenyl)-4,4-difluoro-1,3,5,7-tetramethyl-3a,4a-diaza-4-bora-s-indacene)

Scheme 3:

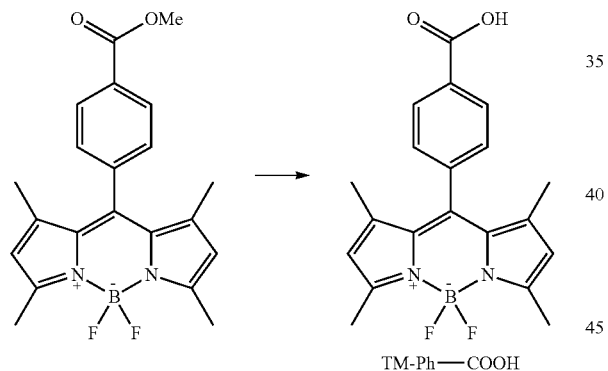

(a) LiOH·H$_2$O; (b) purification by silica flash chromatography (diethyl ether/ethyl acetate/acetone 4.5:4.5:1, v/v)

In a 2-necked flask, 80 mg (0.21 mmol, 1 eq.) of TM-Ph-COOMe were dissolved in 2.5 mL of THF. To this solution, 44.4 mg (1.05 mmol, 5 eq.) of lithium hydroxide monohydrate dissolved in 1 mL of water were rapidly added drop wise. The reaction mixture was kept under stirring for 3 hours at room temperature. Then, it was diluted with a 0.1 M solution of hydrochloric acid and extracted three times with dichloromethane; the combined organic phases were dried on sodium sulfate, filtered and evaporated under reduced pressure. The resulting mixture was purified by means of flash chromatography on silica gel using a diethyl ether/ethyl acetate/acetone mixture (4.5:4.5:1, v/v), affording 17 mg of an orange solid (yield 22%).

$^1$H NMR (CDCl$_3$, 200 MHz, 25° C.) δ: 8.28 (d, J=8.4 Hz, 2H), 7.62 (d, J=8.4 Hz, 2H), 6.17 (s, 2H), 2.54 (s, 6H), 1.44 (s, 6H).

Example 4

Bodipy TM-Ph triethoxysilane (4,4-difluoro-1,3,5,7-tetramethyl-8-(4-((3-(triethoxysilyl)propyl)carbamoyl)phenyl)-3a,4a-diaza-4-bora-s-indacene), B2

Scheme 4:

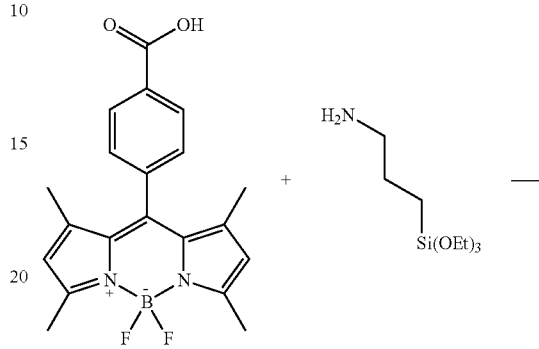

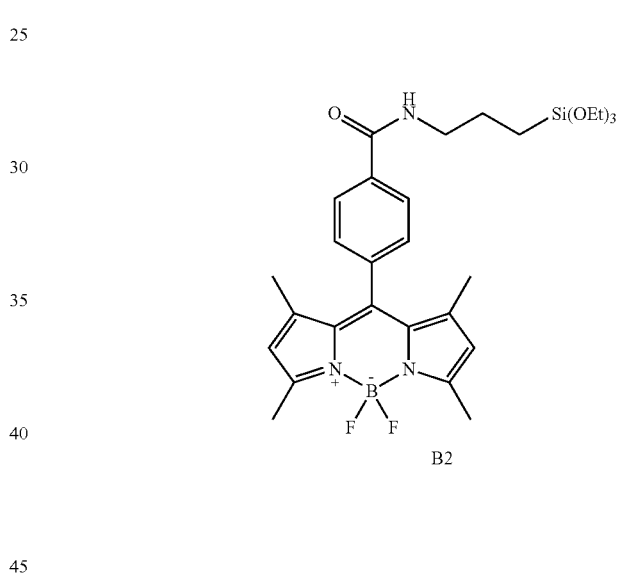

B2

(a) APTES, TEA, EDC, HOBt, dichloromethane; (b) purification by silica flash chromatography (cyclohexane/ethyl acetate 8:2, v/v)

Under a nitrogen atmosphere, 19 μL of 3-aminopropyltriethoxysilane (APTES, 0.079 mmol, 2 eq.), 14.5 mg of TM-Ph-COOH (0.039 mmol, 1 eq.), 11 μL of triethylamine (TEA, 0.079 mmol, 2 eq.), 14.4 μL of N-(3-dimethylaminopropyl)-N'-ethylcarbodiimide (EDC, 0.079 mmol, 2 eq.) and 11 mg of 1-hydroxybenzotriazole hydrate (HOBt, 0.079 mmol, 2 eq.) were dissolved in dichloromethane and stirred overnight at room temperature.

The reaction mixture was then concentrated under reduced pressure and purified by means of flash chromatography on silica using a cyclohexane/ethyl acetate mixture (8:2, v/v) as eluent, obtaining 13.1 mg of the product as a orange-golden solid (yield 58%).

$^1$H NMR (CDCl$_3$, 200 MHz, 25° C.) δ: 7.94 (d, J=8.2 Hz, 2H), 7.39 (d, J=8.2 Hz, 2H), 6.70 (bs, 1H), 5.99 (s, 2H), 3.85 (q, J=7.0 Hz, 6H), 3.57-3.48 (m, 2H), 2.56 (s, 6H), 1.89-1.74 (m, 2H), 1.37 (s, 6H), 1.24 (t, J=7.0 Hz, 9H), 0.76 (t, J=7.9 Hz, 2H).

Example 5

Bodipy TM-Et-COOMe (4,4-difluoro-8-(3-methoxy-3-oxopropyl)-1,3,5,7-tetramethyl-3a,4a-diaza-4-bora-s-indacene)

Scheme 5:

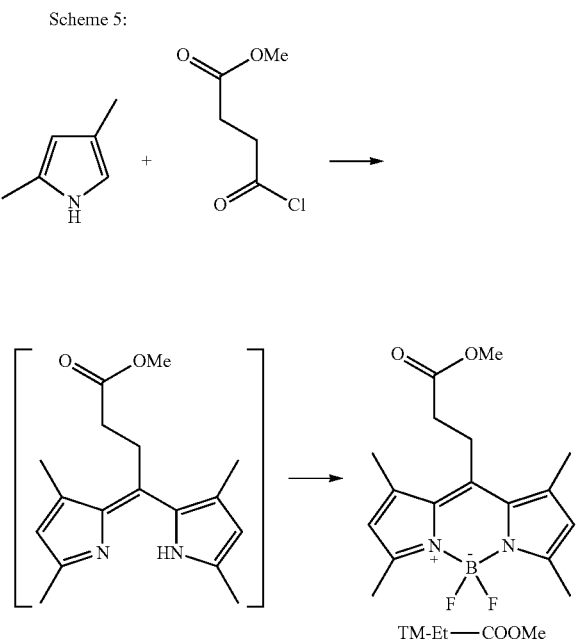

(a) reflux; (b) DIPEA, BF$_3$·Et$_2$O, reflux; (c) purification by silica flash chromatography (cyclohexane/diethyl ether gradient 9:1-8:2, v/v)

Under a nitrogen atmosphere, in a 3-necked flask equipped with a condenser and a dropping funnel, 1000 μL (9.42 mmol, 2 eq.) of 2,4-dimethylpyrrole were dissolved in 12 mL of dichloromethane. To this solution, 1.20 mL (9.42 mmol, 2 eq.) of methyl 4-chloro-4-oxobutyrate, solubilized in 6 mL of dichloromethane, were added drop wise over 30 minutes. The reaction mixture was heated to reflux overnight, during which it assumed a deep purple colour, and then cooled at room temperature. Then 3.68 mL (20.7 mmol, 4.4 eq.) of N,N-diisopropylethylamine and—after 15 minutes—3.84 mL (31.1 mmol, 6.6 eq.) of boron trifluoride diethyl etherate were added. The reaction mixture was again heated to reflux for 3 hours, during which fluorescence appeared.

Finally, the solution was diluted with water and extracted two times with dichloromethane; the combined organic phases were dried on sodium sulfate and evaporated under reduced pressure. The resulting mixture was purified by means of flash chromatography on silica gel using a cyclohexane/ether gradient (9:1-8:2, v/v) as eluent, affording 471 mg of an orange solid (yield 30%).

$^1$H NMR (CDCl$_3$, 400 MHz, 25° C.) δ: 6.05 (s, 2H), 3.72 (s, 3H), 3.31-3.27 (m, 2H), 2.61-2.57 (m, 2H), 2.50 (s, 6H), 2.42 (s, 6H).

Example 6

Bodipy TM-Et-COOH (8-(2-carboxyethyl)-4,4-difluoro-1,3,5,7-tetramethyl-3a,4a-diaza-4-bora-s-indacene)

Scheme 6:

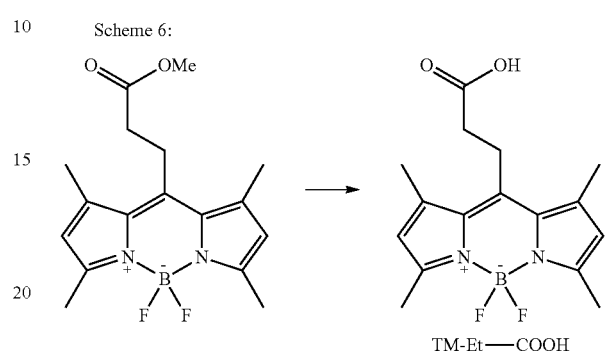

(a) LiOH; (b) purification by silica flash chromatography (cyclohexane/ethyl acetate 3:7, v/v)

In a 2-necked flask, 100 mg (0.30 mmol, 1 eq.) of TM-Et-COOMe were dissolved in 10 mL of THF. To this solution, 36.6 mg (1.5 mmol, 5 eq.) of lithium hydroxide dissolved in 4 mL of water were rapidly added drop wise. The reaction mixture was kept under stirring for 3 hours at room temperature. Then, it was diluted with a 0.1 M solution of hydrochloric acid and extracted three times with dichloromethane; the combined organic phases were dried on sodium sulfate, filtered and evaporated under reduced pressure. The resulting mixture was purified by means of flash chromatography on silica gel using a cyclohexane/ethyl acetate mixture (3:7, v/v), affording 73 mg of an orange solid (yield 76%).

$^1$H NMR (CDCl$_3$, 400 MHz, 25° C.) δ: 6.06 (s, 2H), 3.33-3.29 (m, 2H), 2.67-2.63 (m, 2H), 2.51 (s, 6H), 2.43 (s, 6H).

Example 7

Bodipy TM-Et triethoxysilane (4,4-difluoro-1,3,5,7-tetramethyl-8-(3-oxo-3-((3-(triethoxy-silyl)propyl)amino)propyl)-3a,4a-diaza-4-bora-s-indacene), B1

Scheme 7:

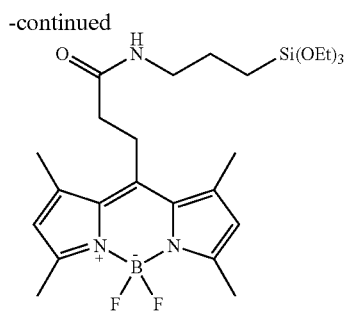

B1

(a) APTES, TEA, EDC, HOBt, dichloromethane; (b) purification by silica flash chromatography (cyclohexane/ethyl acetate gradient 9:1-1:1 v/v)

Under a nitrogen atmosphere, 102 µL of 3-aminopropyltriethoxysilane (APTES, 0.43 mmol, 2 eq.), 68.6 mg of TM-Et-COOH (0.21 mmol, 1 eq.), 59.9 µL of triethylamine (TEA, 0.43 mmol, 2 eq.), 117 µL of N-(3-dimethylaminopropyl)-N'-ethylcarbodiimide (EDC, 0.43 mmol, 2 eq.) and 89.5 mg of 1-hydroxybenzotriazole hydrate (HOBt, 0.43 mmol, 2 eq.) were dissolved in dichloromethane and stirred for 4 hours at room temperature.

The reaction mixture was then concentrated under reduced pressure and purified by means of flash chromatography on silica using a cyclohexane/ethyl acetate gradient (9:1-1:1, v/v) as eluent, obtaining 75.7 mg of the product as a orange-golden solid (yield 68%).

$^1$H NMR (CDCl$_3$, 400 MHz, 25° C.) δ: 6.03 (s, 2H), 5.82 (bs, 1H), 3.79 (q, J=7.1 Hz, 6H), 3.33-3.29 (m, 2H), 3.27-3.22 (m, 2H), 2.49 (s, 6H), 2.42 (s, 6H), 2.41-2.38 (m, 2H), 1.65-1.57 (m, 2H), 1.20 (t, J=7.1 Hz, 9H), 0.60 (t, J=8.0, 2H).

Example 8

Coumarin 343-triethoxysilane (11-oxo-N-(3-(triethoxysilyl)propyl)-2,3,5,6,7,11-hexahydro-1H-pyrano[2,3-f]pyrido[3,2,1-ij]quinoline-10-carboxamide), D2

Scheme 8:

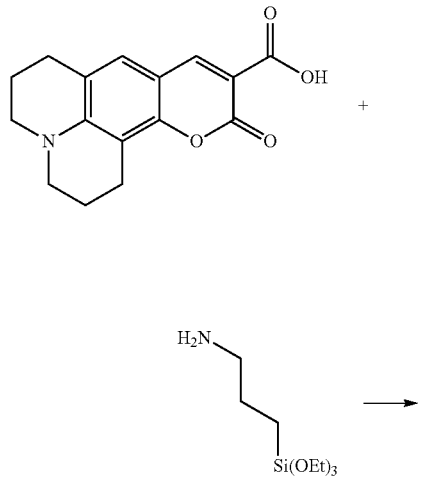

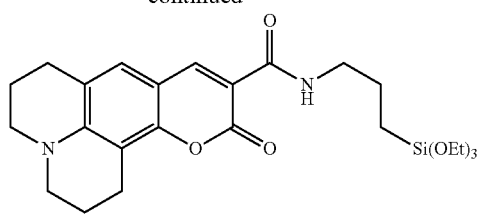

D2

(a) APTES, TEA, EDC, HOBt, dicloromethane; (b) purification by silica flash chromatography (cyclohexane/ethyl acetate gradient 6:4-1:1, v/v)

Under a nitrogen atmosphere, 32.5 µL of 3-aminopropyltriethoxysilane (APTES, 0.136 mmol, 2 eq.), 20 mg of coumarin 343 (0.068 mmol, 1 eq.), 19.1 µL of triethylamine (TEA, 0.136 mmol, 2 eq.), 24.8 µL of N-(3-dimethylaminopropyl)-N'-ethylcarbodiimide (EDC, 0.136 mmol, 2 eq.) and 18.9 mg of 1-hydroxybenzotriazole hydrate (HOBt, 0.136 mmol, 2 eq.) were dissolved in dichloromethane and stirred overnight at room temperature. The reaction mixture was then concentrated under reduced pressure and purified by means of flash chromatography on silica using a cyclohexane/ethyl acetate gradient (6:4-1:1, v/v) as eluent, obtaining 22.8 mg of the product as a light orange solid (yield 69%).

$^1$H NMR (CDCl$_3$, 200 MHz, 25° C.) δ 8.9 (bs, 1H), 8.63 (s, 1H), 7.02 (s, 1H), 3.84 (q, J=7.0 Hz, 6H), 3.50-3.40 (m, 2H), 3.38-3.23 (m, 4H), 2.91-2.76 (m, 4H), 2.05-2.00 (m, 4H), 1.79-1.67 (m, 2H), 1.24 (t, J=7.0 Hz, 9H), 0.72 (t, J=8.4 Hz, 2H).

Example 9

Bodipy TMDE-Ph-COOMe (2,6-diethyl-4,4-difluoro-8-(4-(methoxycarbonyl)-phenyl)-1,3,5,7-tetramethyl-3a,4a-diaza-4-bora-s-indacene)

Scheme 9:

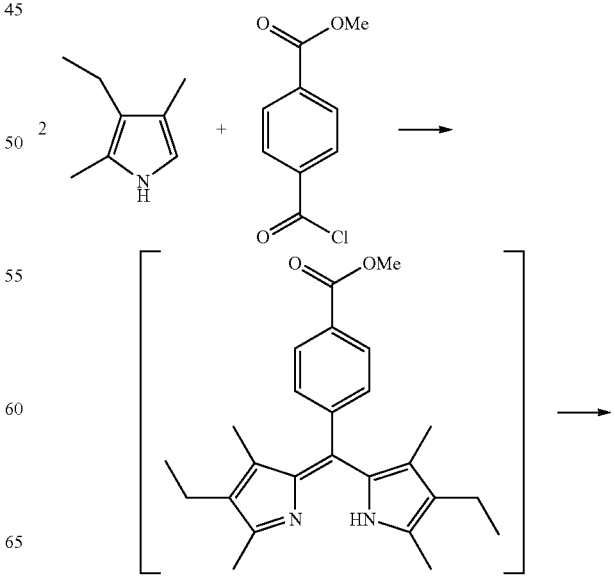

-continued

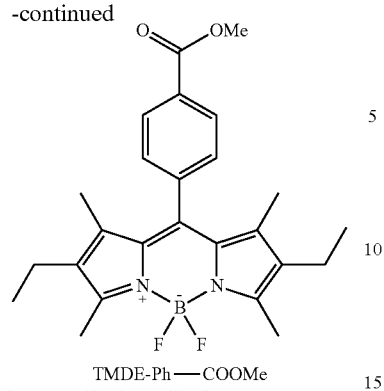

TMDE-Ph—COOMe (a) reflux; (b) DIPEA, BF$_3$•Et$_2$O, reflux; (c) purification by silica flash chromatography (cyclohexane/diethyl ether gradient 98:2-95:5-9:1, v/v)

Under a nitrogen atmosphere, in a 3-necked flask equipped with a condenser and a dropping funnel, were dissolved 602 μL (4.33 mmol, 2 eq.) of 3-ethyl-2,4-dimethylpyrrole and 579 mg (4.76 mmol, 2.2 eq.) of magnesium sulfate in 6 mL of dichloromethane. To this solution, 498 mg (2.38 mmol, 1.1 eq.) of methyl 4-(chlorocarbonyl)benzoate, solubilized in 4 mL of dichloromethane, were added drop wise over 30 minutes. The reaction mixture was heated to reflux for 3 hours, during which it assumed a deep purple colour, and then cooled at room temperature. Then 1.69 mL (9.53 mmol, 4.4 eq.) of N,N-diisopropylethylamine and—after 15 minutes—1.76 mL (14.3 mmol, 6.6 eq.) of boron trifluoride diethyl etherate were added. The reaction mixture was again heated to reflux for 3 hours, during which fluorescence appeared.

Finally, the solution was diluted with water and extracted two times with dichloromethane; the combined organic phases were dried on sodium sulfate and evaporated under reduced pressure. The resulting mixture was purified by means of flash chromatography on silica gel using a cyclohexane/ether gradient (98:2-95:5-9:1, v/v) as eluent, affording 411 mg of a dark orange solid (yield 44%).

$^1$H NMR (CDCl$_3$, 200 MHz, 25° C.) δ 8.18 (d, J=8.6 Hz, 2H), 7.42 (d, J=8.6 Hz, 2H), 3.99 (s, 3H), 2.54 (s, 6H), 2.30 (q, J=7.5 Hz, 4H), 1.26 (s, 6H), 0.96 (t, J=7.5 Hz, 6H).

Example 10

Bodipy TMDE-Ph-COOH (8-(4-carboxyphenyl)-2,6-diethyl-4,4-difluoro-1,3,5,7-tetramethyl-3a,4a-diaza-4-bora-s-indacene)

Scheme 10:

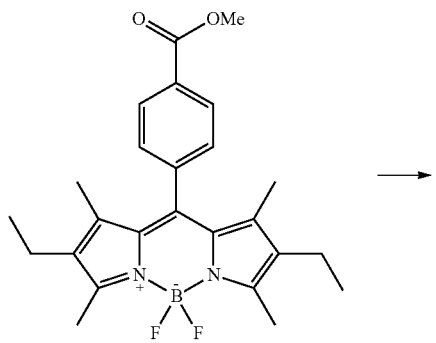

-continued

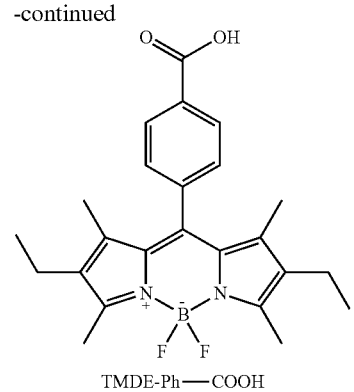

TMDE-Ph—COOH (a) LiOH•H$_2$O; (b) purification by silica flash chromatography (diethyl ether/ethyl acetate/acetone 4.5:4.5:1, v/v)

In a 2-necked flask, 100 mg (0.23, 1 eq.) of Bodipy TMDE-Ph-COOMe were dissolved in 2.5 mL of THF. To this solution were rapidly added drop wise a 1 mL water solution containing 48.3 mg (1.14, 5 eq.) of lithium hydroxide monohydrate. The reaction mixture was kept under stirring for 5 hours at room temperature. Then, it was diluted with water and extracted three times with ethyl acetate; the combined organic phases were dried on sodium sulfate, filtered and evaporated under reduced pressure. The resulting mixture was purified by means of flash chromatography on silica gel using a diethyl ether/ethyl acetate/acetone mixture (4.5:4.5:1, v/v), affording 41 mg of an orange solid (yield 42%).

$^1$H NMR (CDCl$_3$, 200 MHz, 25° C.) δ 8.26 (d, J=8.4 Hz, 2H), 7.46 (d, J=8.4 Hz, 2H), 2.55 (s, 6H), 2.31 (q, J=7.5 Hz, 4H), 1.28 (s, 6H), 0.99 (t, J=7.5 Hz, 6H).

Example 11

Bodipy TMDE-Ph triethoxysilane (2,6-diethyl-4,4-difluoro-1,3,5,7-tetramethyl-8-(4-((3-(triethoxysilyl)propyl)carbamoyl)phenyl)-3a,4a-diaza-4-bora-s-indacene), B Scheme 11:

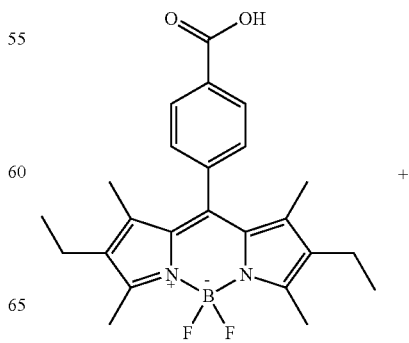

+

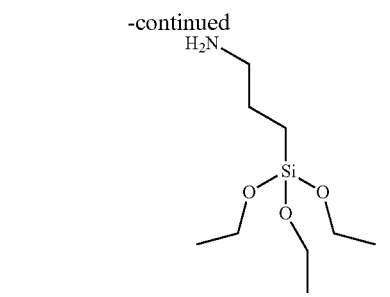

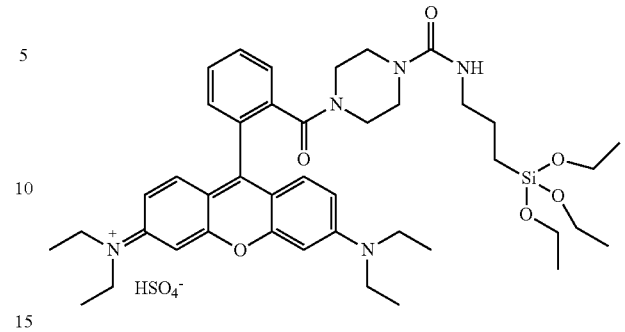

Scheme 12: rhodamine B triethoxysilane derivarive, R

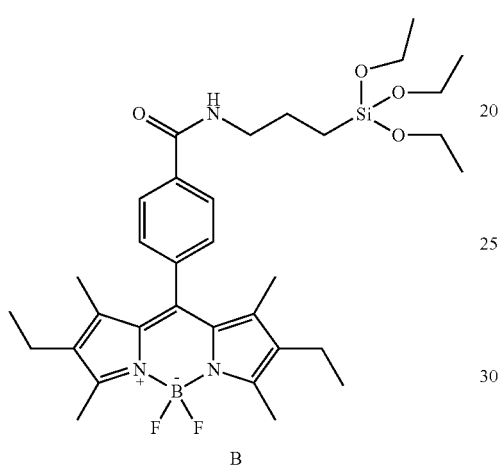

B (a) APTES, TEA, EDC, HOBt, dichloromethane; (b) purification by silica flash chromatography (cyclohexane/diethyl ether 1:1, v/v)

Under a nitrogen atmosphere, 17 μL of 3-aminopropyl-triethoxysilane (APTES, 0.07 mmol, 2 eq.), 15 mg of Bodipy TMDE-Ph-COOH (0.035 mmol, 1 eq.), 10 μL of triethylamine (TEA, 0.07 mmol, 2 eq.), 13 mg of N-(3-dimethylaminopropyl)-N'-ethylcarbodiimide (EDC, 0.07 mmol, 2 eq.) and 10 mg of 1-hydroxybenzotriazole hydrate (HOBt, 0.07 mmol, 2 eq.) were dissolved in dichloromethane and stirred overnight at room temperature.

The reaction mixture was then concentrated under reduced pressure and purified by means of flash chromatography on silica using a cyclohexane/diethyl ether mixture (1:1, v/v) as eluent, obtaining 15.1 mg of the product as a orange-golden solid (yield 68%).

$^1$H NMR (CDCl$_3$, 200 MHz, 25° C.) δ 7.94 (d, J=8.2 Hz, 2H), 7.39 (d, J=8.2 Hz, 2H), 6.70 (bs, 1H), 3.86 (q, J=7.1 Hz, 6H), 3.53 (q, J=6.3 Hz, 2H), 2.54 (s, 6H), 2.31 (q, J=7.6 Hz, 4H), 1.89-1.75 (m, 2H), 1.28-1.21 (m, 15H), 0.99 (t, J=7.6 Hz, 6H), 0.77 (t, J=7.9 Hz, 2H).

Example 12

Synthesis of the Rhodamine B Triethoxysilane Derivarive, R

The rhodamine B derivative R was synthesized using reported procedures. [*J. Phys. Chem. B*, 2010, 114(45), 14606-14613.]

Example 13

DEAC triethoxysilane. Synthesis of 7-(diethyl-amino)-N-(3-(triethoxysilyl)propyl)-2-oxo-2H-chromene-3-carboxamide (7-(diethylamino)-N-(3-(triethoxysilyl)-propyl)coumarin-3-carboxamide), D Under a nitrogen atmosphere, 34 μL of 3-aminopropyl-triethoxysilane (APTES, 0.14 mmol, 2 eq.), 19 mg of 7-(diethylamino)coumarin-3-carboxylic acid (DEAC, 0.07 mmol, 1 eq.), 20 μL of triethylamine (TEA, 0.14 mmol, 2 eq.), 26 mg of N-(3-dimethylaminopropyl)-N'-ethylcarbodiimide (EDC, 0.14 mmol, 2 eq.) and 20 mg of 1-hydroxybenzotriazole hydrate (HOBt, 0.14 mmol, 2 eq.) were dissolved in dichloromethane and stirred overnight at room temperature.

Scheme 13:

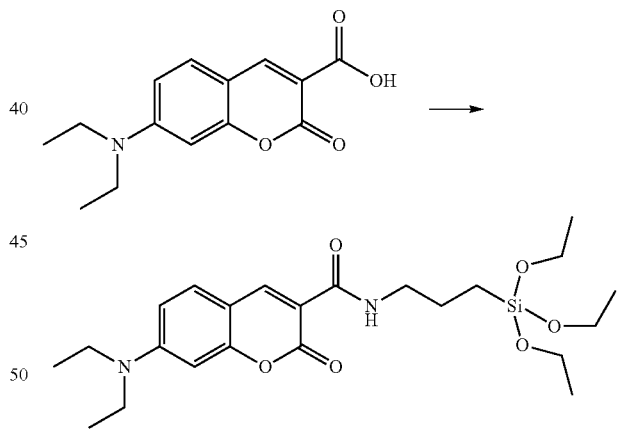

D (a) APTES, TEA, EDC, HOBt, dichloromethane; (b) purification by silica flash chromatography (cyclohexane/ethyl acetate 1:1, v/v)

The reaction mixture was then concentrated under reduced pressure and purified by means of flash chromatography on silica using a cyclohexane/ethyl acetate mixture (1:1, v/v) as eluent, obtaining 15.7 mg of the product as a yellow solid (yield 48%).

$^1$H NMR (CDCl$_3$, 200 MHz, 25° C.) δ 8.81-8.85 (m, 1H), 8.71 (s, 1H), 7.43 (d, J=8.8 Hz, 1H), 6.65 (dd, J=2.5 Hz, J=8.8 Hz, 1H), 6.51 (d, J=2.5 Hz, 1H), 3.83 (q, J=6.9 Hz, 6H), 3.40-3.51 (m, 6H), 1.66-1.82 (m, 2H), 1.20-1.28 (m, 15H), 0.67-0.76 (m, 2H).

ESI-MS (M+H$^+$)=465.

Example 14

Triethoxysilane Derivative of Chromis 800 C NHS, C7

Scheme 14: APTES, dichloromethane.

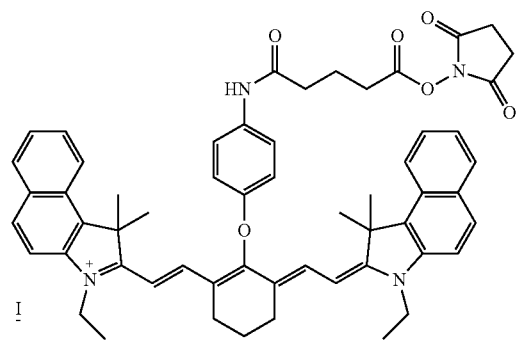

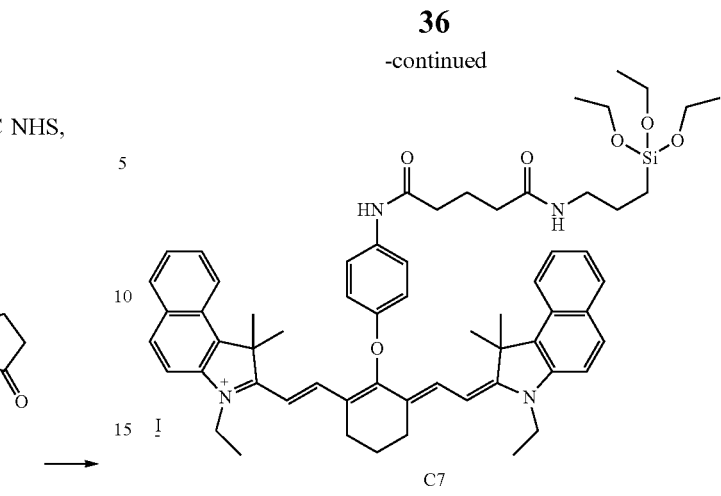

In a glass vial 0.82 mg of Chromis 800 C NHS (0.0008 mmol, 1 eq.) were solubilised with 245 µL of dry dichloromethane. To this solution were added 3.8 µL of a 1:10 (v/v) solution of APTES in dichloromethane (0.0016 mmol, 2 eq.). The mixture was stirred overnight and then used without further purification.

Example 15

Triethoxysilane Derivative of Chromis 830 a NHS, C2

Scheme 15: APTES, dichloromethane.

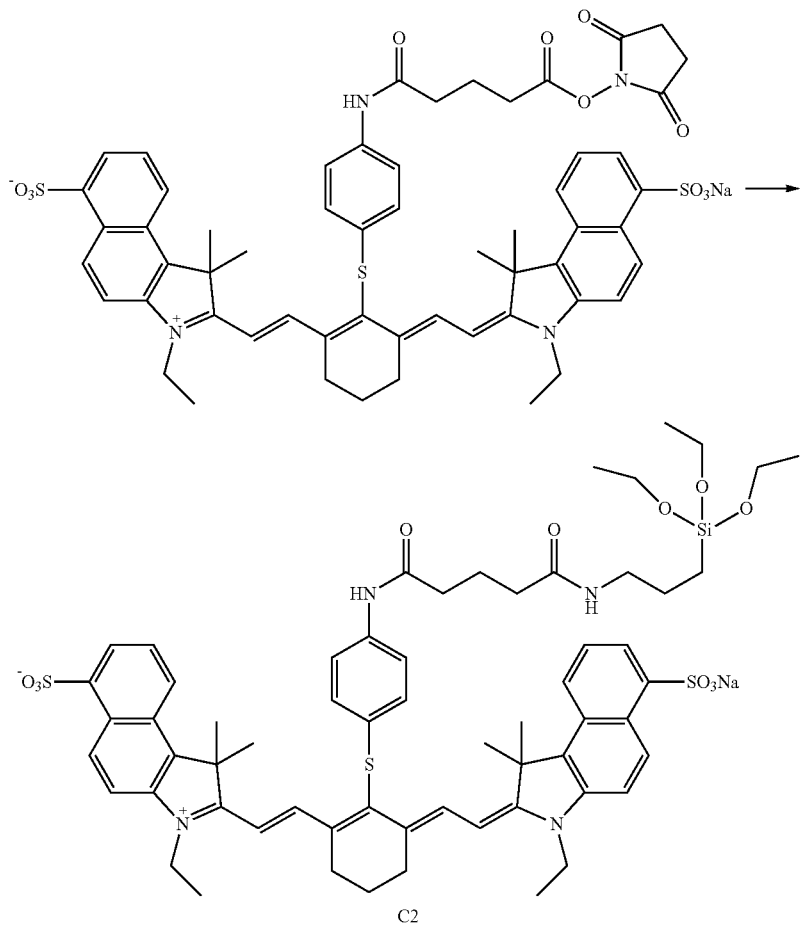

In a glass vial 0.88 mg of Chromis 800 C NHS (0.0008 mmol, 1 eq.) were solubilised with 245 µL of dry dichloromethane. To this solution were added 3.8 µL of a 1:10 (v/v) solution of APTES in dichloromethane (0.0016 mmol, 2 eq.). The mixture was stirred overnight and then used without further purification.

Example 16

Nanoparticles Synthesis

Core-shell silica-PEG (polyethylene glycol) nanoparticles were synthesized adapting previously reported procedures. [*J. Phys. Chem. B*, 2010, 114(45), 14605-14613] In a typical preparation 100 mg of Pluronic F127 and the desired amount of the silanized or water insoluble dye/s were carefully solubilized with 1.0-2.0 mL of dichloromethane in a 20 mL glass scintillation vial. The solvent was evaporated from the homogeneous solution by means of a gently nitrogen flow and subsequently under vacuum at room temperature. NaCl (68.6 mg) was added to the solid residue and the mixture was solubilized at 25° C. under magnetic stirring with 1565 µL of acetic acid 1 M. TEOS (179 µL, 0.80 mmol) was then added to the resulting aqueous homogeneous solution followed by TMSCl (10 µL, 0.08 mmol) after 180 min.

The mixture was kept under stirring for 48 h at 25° C. before dialysis treatments. The dialysis purification steps were carried out versus water on a precise amount of nanoparticles solution (1500 µL) finally diluted to a total volume of 5 mL with water.

Example 17

Alternative Synthetic Scheme that can be Used, Especially with Dyes not Stable in Acidic Environment In a typical preparation 100 mg of Pluronic F127 and the desired amount of the silanized or water insoluble dye/s were carefully solubilized with 1.0-2.0 mL of dichloromethane in a 20 mL glass scintillation vial. The solvent was evaporated from the homogeneous solution by means of a gently nitrogen flow and subsequently under vacuum at room temperature. NaCl (68.6 mg) was added to the solid residue and the mixture was solubilized at 25° C. under magnetic stirring with 1565 µL of water. TMOS (119 µL, 0.8 mmol) was then added to the resulting aqueous homogeneous solution followed by TMSCl (10 µL, 0.08 mmol) after 15 min.

The mixture was kept under stirring for 48 h at 25° C. before dialysis treatments. The dialysis purification steps were carried out versus water on a precise amount of nanoparticles solution (1500 µL) finally diluted to a total volume of 5 mL with water.

DLS:

the determination of the nanoparticles hydrodynamic diameter distributions was carried out through Dynamic Light Scattering measurements employing a Malvern Nano ZS instrument equipped with a 633 nm laser diode. Samples were housed in disposable polystyrene cuvettes of 1 cm optical path length, using water as solvent. The width of DLS hydrodynamic diameter distribution is indicated by PdI (Polydispersion Index). In case of a mono-modal distribution (gaussian) calculated by means of cumulant analysis, $PdI=(\sigma/Z_{avg})^2$, where $\sigma$ is the width of the distribution and $Z_{avg}$ is the average diameter of the particles population respectively.

TEM Experiments:

A Philips CM 100 transmission electron microscope operating at 80 kV was used. For TEM investigations a 3.05 mm copper grid (400 mesh) covered by a Formvar support film was dried up under vacuum after deposition of a drop of nanoparticles solution diluted with water (1:50).

Figure 2:
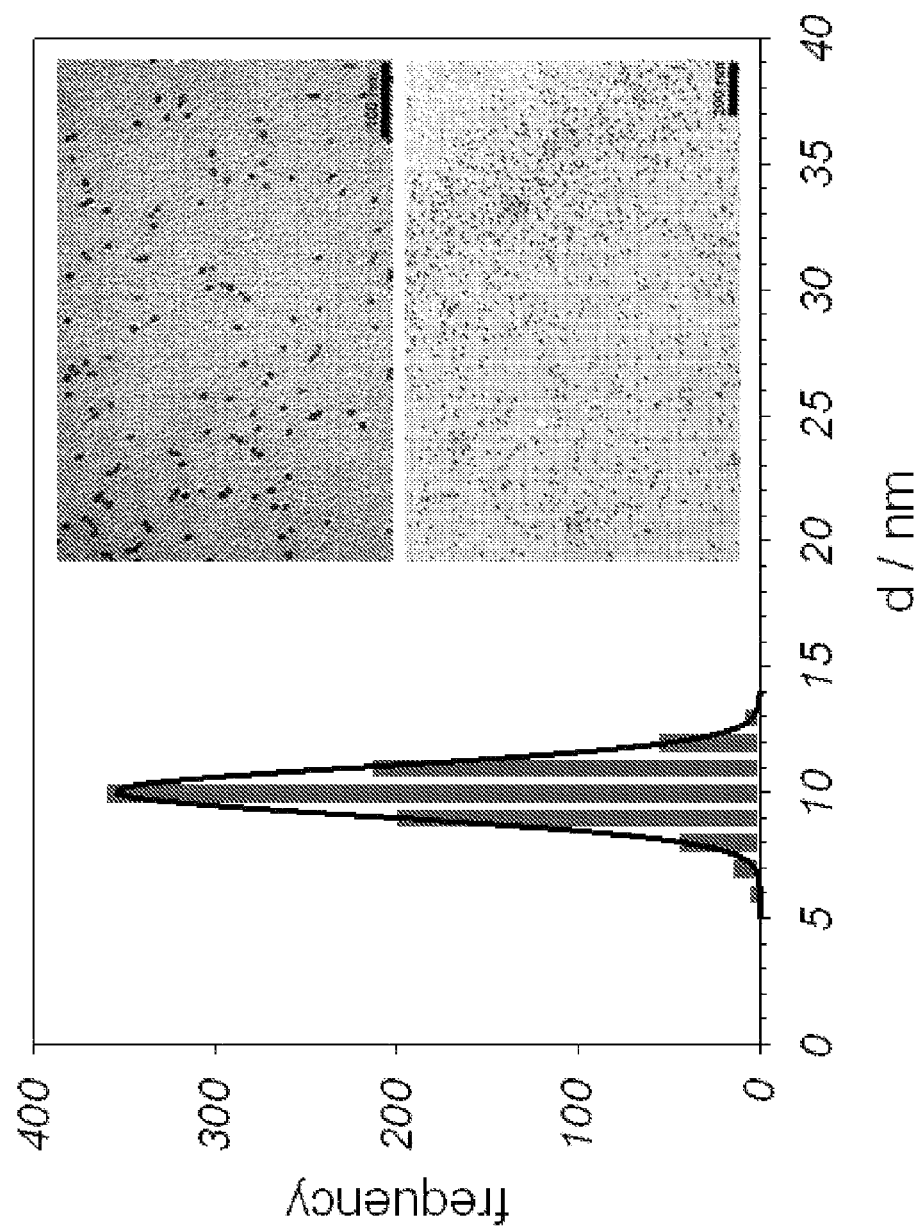
FIG. 2 shows the typical TEM images of core-shell silica-PEG nanoparticles, and silica core size distribution, d=(11±3) nm, (scale bars 100 nm and 200 nm).
Figure 3:
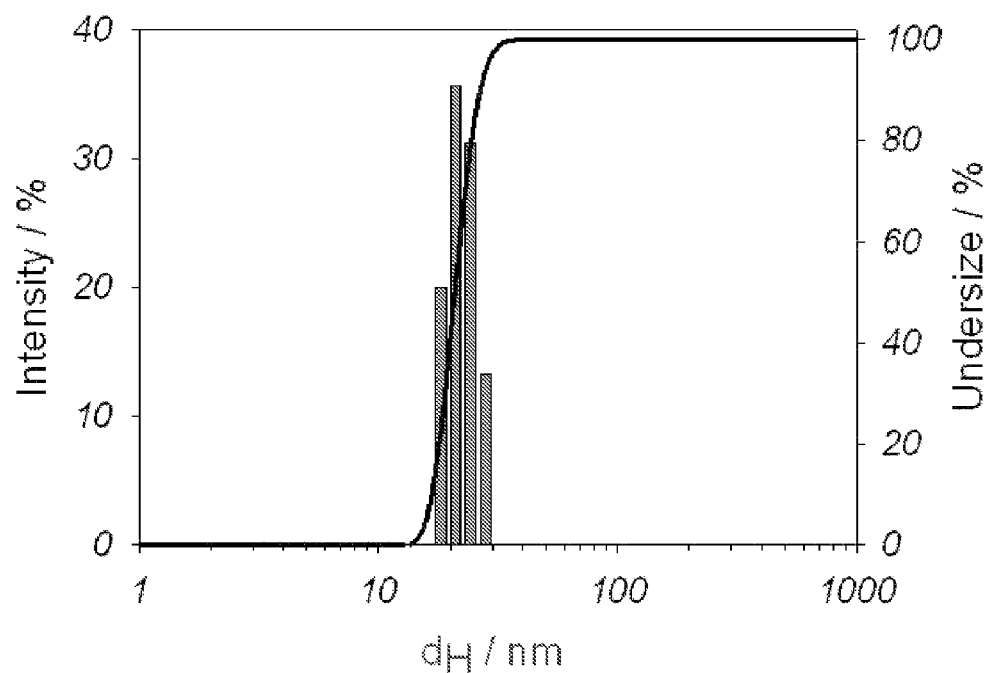
FIG. 3 shows the typical Dynamic light scattering diameter distribution of core-shell silica-PEG nanoparticles (d=23 nm, PdI=0.09) in water.

The NPs TEM images show that only the silica cores present sufficient contrast to appear in the images. The size distribution was obtained analyzing images with a block of several hundred nanoparticles, FIG. 2 (left). The obtained histogram was fitted according to a Gaussian distribution obtaining an average diameter of (11±3) nm for the silica nanoparticles core.

Photophysical Measurements:

All the NPs solutions show very weak light scattering and can be treated from the photophysical point of view as any solution of molecular species. DLS measurements show no aggregation of the NPs even after several months.

UV-VIS absorption spectra were recorded at 25° C. by means of Perkin-Elmer Lambda 45 spectrophotometer. Quartz cuvettes with optical pathlength of 1 cm were used. The fluorescence spectra were recorded with an Edinburgh FLS920 equipped photomultiplier Hamamatsu R928P. The same instrument connected to a PCS900 PC card was used for the Time Correlated Single Photon Counting (TCSPC) experiments. Luminescence quantum yields (uncertainty, ±15%) were determined using solutions of rhodamine 6G in ethanol as a reference ($\phi$=0.94), and fluorescence intensities were corrected for inner filter effects according to standard methods. [Montalti, M.; Credi, C.; Prodi, L.; Gandolfi, M. T. *Handbook of Photochemistry*, CRC Press Boca Raton (Fla.), 2006.].

All fluorescence anisotropy measurements were performed on an Edinburgh FLS920 equipped with Glan-Thompson polarizers. Anisotropy measurements were collected using an L-format configuration and all data were corrected for polarization bias using the G-factor.

Four different spectra were acquired for each sample combining different orientation of the excitation and emission polarizers: $I_{VV}$, $I_{VH}$, $I_{HH}$, $I_{HV}$ (where V stands for vertical and H for horizontal; the first subscript is referred to the excitation and the second to the emission). The spectra were used to calculate the G-factor and the anisotropy

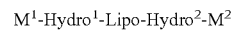

$G=I_{HV}/I_{HH}, r=(I_{VV}-GI_{VH})/I_{VV}+2GI_{VH}$.

[Lakowicz, J. R., Principles of Fluorescence Spectroscopy, Third Edition, Lakowicz, J. R., Springer 2006.]

The invention claimed is:

1. A silica nanoparticle comprising
   a. a micelle, said micelle having a substantially hydrophilic shell and a substantially hydrophobic central portion;
   b. a core, which is located in the area of the micelle central portion and comprises a silicate network;
   c. a plurality of molecules of at least a surfactant, which molecules comprise at least a molecule of a functionalized surfactant having the following structure:

$M^1$-Hydro$^1$-Lipo-Hydro$^2$-$M^2$ wherein
   Lipo represents a substantially hydrophobic chain,
   Hydro$^1$ and Hydro$^2$ represent, independently of each other, a respective substantially hydrophilic chain;
   $M^1$ is a recognition functionality, wherein said functionality is selected from the group consisting of amine, —COOH, —$N_3$, alkyne, alkene, acryloyl, —SH, maleimide, aldehyde, —OH, isothiocyanate, sulfonyl chloride, iodoacetyl, TCT (2,4,6-Trichloro-1,3,5-triazine) and an activated carboxylic group; $M^2$ is selected from the group consisting of: —H, —OH, a recognition functionality and a hetero group; and d. a first and at least a second dye in said core; wherein said first and said at least second dye have a respective relationship of donor-acceptor couple in an energy transfer process and have a molar absorption coefficient $\epsilon \geq 10{,}000$ $M^{-1}$ $cm^{-1}$ for a considered spectral region, a fluorescence quantum yield $\phi \geq 0.01$, an overlap integral, which is an overlap integral J defined according to the Forster theory that is greater than $1 \times 10^{12}$ $M^{-1}cm^{-1}nm^4$, conveniently greater than $1 \times 10^{14}$ $M^{-1}cm^{-1}nm^4$, between said donor and said acceptor dye; said dyes may be lipophilic or may present a functionality useful for the introduction of a trialkoxysilane moiety, and wherein said donor dye is a coumarinic or a xanthene dye.

2. The nanoparticle according to claim 1, wherein said xanthene dye is fluorescein.

3. The nanoparticle according to claim 1, wherein said coumarinic dye comprises 7-(diethylamino)-N-(3-(triethoxysilyl)propyl)-2-oxo-2H-chromene-3-carboxamide (D) or 11-oxo-N-(3-(triethoxysilyl)propyl)-2,3,5,6,7,11-hexahydro-1H-pyrano[2,3-f]pyrido[3,2,1-ij]quinoline-10-carboxamide (D2).

4. The nanoparticle according to claim 1, wherein said acceptor dye is selected from the group consisting of: (2,6-diethyl-4,4-difluoro-1,3,5,7-tetramethyl-8-(4-((3-(triethoxysilyl)propyl) carbamoyl) phenyl)-3a,4a-diaza-4-bora-s-indacene) (B), 4,4-difluoro-1,3,5,7-tetramethyl-8-(3-oxo-3-((3-(triethoxy-silyl)propyl)amino) propyl)-3a,4a-diaza-4-bora-s-indacene (B1), 4,4-difluoro-1,3,5,7-tetramethyl-8-(4-((3-(triethoxysilyl)propyl)carbamoyl)phenyl)- 3a,4a-diaza-4-bora-s-indacene (B2), a Rhodamine B triethoxysilane (R), the triethoxysilane cyanine 2-((1E, 3E,5E)-5-(1-(6-(2,5-dioxopyrrolidin-1-yloxy)-6-oxohexyl)-3,3-dimethylindolin-2-yli-dene)-penta-1,3-dienyl)-1-ethyl-3,3-dimethyl-3H-indolium iodide (C5), the triethoxysilane cyanine 2-((E)-2-((E)-2-(4-(5-(2,5-dioxopyrrolidin-1-yloxy)-5-oxopentanamido)phenoxy)-3-((Z)-2-(3-ethyl-1,1-dimethyl-1H-benzo[e]indol-2(3H)-ylidene)ethylidene)cyclo-hex-1-enyl)vinyl)-3-ethyl-1,1-dimethyl-1H-benzo[e]indolium iodide (C7) and the triethoxysilane derivative of cyanine Sodium 2-((E)-2-((E)-2-(4-(5-(2,5-dioxopyrrolidin-1-yloxy)-5-oxopentanamido) phenylthio)-3-((Z)-2-(3-ethyl-1,1-dimethyl-6-sulfonato-1H-benzo[e]indol-2(3H)-ylidene)ethylidene) cyclohex-1-enyl)vinyl)-3-ethyl-1,1-dimethyl-1H-benzo[e]indolium-6-sulfonate (C2).

5. The nanoparticle according to claim 1, wherein said nanoparticle comprises a combination of dyes selected from the group consisting of DB, DR, DC5, DBR, DBC5, DRC5, DBRC5, DBRC5C7 and D2B2C5C2.

6. The nanoparticle according to claim 1, wherein said nanoparticle comprises a combination of dyes selected from the group consisting of BR, BC5, RC5, and BRCS.

7. A probe for use in at least one of therapy, diagnostics, theranostics, and analytical chemistry comprising at least one nanoparticle according to claim 1.

8. A diagnostic or theranostic composition comprising a suitable amount of the nanoparticle of claim 1.

9. The nanoparticle according to claim 1, wherein said activated carboxylic group is selected from the group consisting of NHS and NHS-sulfo esters (N-hydroxysuccinimide and sulfo N-hydroxysuccinimide), TFP ester (2,3,5,6-Tetrafluorophenol), PFP ester (pentafluorophenol), HOBt ester (1-hydroxybenzotriazole), N-acylimidazole.

\* \* \* \* \*